(12) United States Patent
Nygaard et al.

(10) Patent No.: US 8,815,276 B2
(45) Date of Patent: Aug. 26, 2014

(54) THREE-DIMENSIONAL NANOSTRUCTURED HYBRID SCAFFOLD AND MANUFACTURE THEREOF

(75) Inventors: Jens Vinge Nygaard, Hjortshøj (DK); Lea Bjerre, Hørsholm (DK); Cody Eric Bünger, Auning (DK); Flemming Besenbacher, Århus V (DK)

(73) Assignees: Aarhus Universitet, Arhus C. (DK); Region Midtjylland, Viborg (DK)

( * ) Notice: Subject to any disclaimer, the term of this patent is extended or adjusted under 35 U.S.C. 154(b) by 0 days.

(21) Appl. No.: 13/377,430

(22) PCT Filed: Jun. 25, 2010

(86) PCT No.: PCT/DK2010/050167
§ 371 (c)(1),
(2), (4) Date: Jan. 31, 2012

(87) PCT Pub. No.: WO2010/149176
PCT Pub. Date: Dec. 29, 2010

(65) Prior Publication Data
US 2012/0128739 A1    May 24, 2012

(30) Foreign Application Priority Data
Jun. 26, 2009  (EP) .................................... 09163896

(51) Int. Cl.
*A61F 2/00* (2006.01)

(52) U.S. Cl.
USPC ........................................... 424/423; 424/424

(58) Field of Classification Search
None
See application file for complete search history.

(56) References Cited

U.S. PATENT DOCUMENTS

| | | | | |
|---|---|---|---|---|
| 6,103,255 | A * | 8/2000 | Levene et al. | 424/426 |
| 2005/0079200 | A1 | 4/2005 | Rathenow et al. | |
| 2006/0115514 | A1 | 6/2006 | Gengrinovitch | |
| 2008/0033548 | A1 * | 2/2008 | Xuenong et al. | 623/11.11 |
| 2009/0155334 | A1 * | 6/2009 | Mallick et al. | 424/423 |

FOREIGN PATENT DOCUMENTS

| | | |
|---|---|---|
| DE | 103 22 182 A1 | 12/2004 |
| WO | WO 03/026714 A1 | 4/2003 |

OTHER PUBLICATIONS

Guarino, V. et al., "Design and manufacture of microporous polymeric materials with hierarchal complex structure for biomedical application" Materials Science and Technology, Sep. 2008, pp. 1111-1117, vol. 24, No. 9.
Heijkants, R. G. J. C., et al., "Preparation of a polyurethane scaffold for tissue engineering made by a combination of salt leaching and freeze-drying of dioxane" J Mater Sci, 2006, pp. 2423-2428, vol. 41.
Heijkants, R. G. J. C., et al., "Polyurethane scaffold formation via a combination of salt leaching and thermally induced phase separation" Journal of Biomedical Materials Research, 2008, pp. 921-932.
Hua, Feng Jun et al., "Macroporous Poly(L-lactide) Scaffold 1. Preparation of a Macroporous Scaffold by Liquid-Liquid Phase Separation of a PLLA-Dioxane-Water System" J Biomed Mater Res, 2002, pp. 161-167, vol. 63.
Knackstedt, Mark A. et al., "Elastic and transport properties of cellular solids derived from three-dimensional tomographic images" Proc. R. Soc., 2006, pp. 2833-2862, vol. 462.
Mo, X. et al., "PCL-PGLA composite tubular scaffold preparation and biocompatibility in investigation" The International Journal of Artificial Organs, 2006, pp. 790-799, vol. 29, No. 8.
Odgaard, A. et al., "Quantification of Connectivity in Cancellous Bone, with Special Emphasis on 3-D Reconstructions" Bone, 1993, pp. 173-182, vol. 14.
Parfitt, A.M. et al., "Relationships between Surface, Volume, and Thickness of Iliac Trabecular Bone in Aging and in Osteoporosis; Implications for the Microanatomic and Cellular Mechanisms of Bone Loss" J. Clin. Invest., Oct. 1983, pp. 1396-1409, vol. 72.
Simmons, Craig A. et al., "Method-Based Differences in the Automated Analysis of the Three-Dimensional Morphology of Trabecular Bone" Journal of Bone and Mineral Research, 1997, pp. 942-947, vol. 12, No. 6.

* cited by examiner

*Primary Examiner* — Susan Tran
(74) *Attorney, Agent, or Firm* — Knobbe Martens Olson & Bear LLP

(57) ABSTRACT

A method of making a three-dimensional biocompatible scaffold capable of supporting cell activities such as growth and differentiation, the method includes providing a supporting grid that forms an open network and provides mechanical support of a second biocompatible material. The second biocompatible material has interconnected cavities that allow nutrients, metabolites and soluble factors to diffuse throughout the scaffold. The scaffold design can be understood as a hierarchically organised structure. At the micron to submicron length scale a top/down manufacturing approach is used to make a structure that will constitute the frame into which a bottom/up processing approach is applied to form an open porous scaffold with specific nano sized features. The advantage of this hierarchically organised design is that benefits can be drawn independently from both the micron and the nano sized structures, promoting specific cell activities and providing sufficient mechanical compliance.

15 Claims, 20 Drawing Sheets

THREE-DIMENSIONAL NANOSTRUCTURED HYBRID SCAFFOLD AND MANUFACTURE THEREOF

CROSS REFERENCE TO RELATED APPLICATIONS

This application claims the benefit and priority to and is a U.S. National Phase Application of PCT International Application Number PCT/DK2010/050167, filed on Jun. 25, 2010, designating the United States of America and published in the English language, which is an International Application of and claims the benefit of priority to European Patent Application No. 09163896.5, filed on Jun. 26, 2009. The disclosures of the above-referenced applications are hereby expressly incorporated by reference in their entireties.

TECHNICAL FIELD OF THE INVENTION

The present invention relates to three-dimensional hybrid scaffolds for tissue engineering and methods of their manufacture and use.

BACKGROUND OF THE INVENTION

Tissue engineering is a strategy for repairing or regenerating tissue. Cell culture in the context of tissue engineering further requires a three-dimensional scaffold for cell support. A scaffold having a three-dimensional porous structure is a prerequisite in many tissue culture applications as these cells would otherwise lose their cellular morphology and phenotypic expression in a two-dimensional monolayer cell culture.

An important issue in tissue regeneration and repair is the fabrication of three-dimensional scaffolds in such a manner that they mimic the extracellular matrix and thereby encourage the cells to grow functional tissues and allow the diffusion of nutrients, metabolites and soluble factors.

When regenerating tissue, the properties of the three-dimensional matrix can greatly affect cell adhesion and growth, and determine the quality of the final product. An optimal scaffold material would promote cell adhesion, cell proliferation, expression of cell-specific phenotypes, and the activity of the cells.

Biological materials have been used as scaffolding material in many tissue engineering applications and within the field of regenerative medicine to control the function and structure of engineered tissue by interacting with transplanted cells. These materials include naturally derived materials such as collagen and alginate. Some biological materials have been proven to support cell ingrowth and regeneration of damaged tissues with no evidence of immunogenic rejection, and encourage the remodelling process by stimulating cells to synthesize and excrete extracellular matrix proteins to aid in the healing process. Extracellular matrix components preserved in these biological materials are also able to influence the phenotypic differentiation of stem cells through specific interactions with e.g. cell surface receptors. However, the usage of such isolated biological materials is limited because of insufficient mechanical properties upon implantation and during perfusion cell seeding.

High porosity of the scaffold is generally recommended to reduce the amount of implanted material and to generate a large surface on to which the cells can adhere. Moreover, interconnectivity, the connection between the pores in the scaffold, is very important since it plays a decisive role in cell mobility within the scaffold and afterwards in the transport (diffusion and convection) of nutrients and cellular waste products.

Heijkants et al. (2008) discloses the manufacture of a porous scaffold from polyurethane by a combination of salt leaching and thermally induced phase separation. The method makes it possible to obtain a very porous foam material with a very high interconnectivity. A major advantage is that variables like porosity, pore size, and interconnectivity can be independently adjusted with the absence of toxic materials in the production process. However, an increase in the porosity of the resulting foam decreases the mechanical stability of the scaffold.

WO2006093778 discloses a solid freeform fabrication method of creating a three-dimensional article built at least in part from scaffolding layers. The method includes providing a scaffolding material and a supporting material. The supporting material is in the shape of a foamy layer. The foam is used as a support for the scaffolding material during preparation of the scaffold and subsequently removed by washing. In certain embodiments of the method, the foam is not removed, but is retained within the structure. WO2006093778 states that the problem with retaining the foam within the structure is that it traps air and may be restrictive to cell migration and travel. Additionally, for the printing device to be able to print directly into the foam, the foam has to be pliable for the nozzle of the printing device to be submerged. Therefore, the foam cannot be of the polymer type disclosed in the paper by Heijkants et al.

Mo et al. (2006) discloses a hollow PCL-PLGA composite tubular scaffold for blood vessel tissue engineering. This scaffold comprises a hollow PLGA braided tube coated with PCL; obtained by coating the braided tube with a PCL dioxane/water solution and then freeze-drying after phase separation. The hollow structure of the braided tube makes it especially vulnerable towards compressive forces under preparation, insertion and use.

Thus, it is an object of the present invention to improve the properties of a three-dimensional scaffold for its use in tissue engineering. In particular, an improved mechanical stability of the scaffold would be advantageous. More specifically, an improved compressive mechanical stress of the scaffold under preparation (e.g. cutting), insertion and use (e.g. when implanted) would be advantageous. Furthermore, improved cell mobility within the scaffold and transport of nutrients and cellular waste products would be advantageous.

SUMMARY OF THE INVENTION

An object of the present invention relates to a method of making a three-dimensional biocompatible scaffold capable of supporting cell activities such as growth and differentiation.

In particular, it is an object of the present invention to provide a method that solves the above mentioned problems of the prior art.

Thus, one aspect of the invention relates to a method of making a three-dimensional biocompatible scaffold capable of supporting cell activities such as growth and differentiation, the method comprising providing a supporting grid comprising a first biocompatible material, said grid providing mechanical support of a second biocompatible material, said first material comprising one or more polymers, said grid forming an open network, adding a solution comprising a mixture of one or more biodegradable polymers and two or more solvents to a substantial part of the open network, removing said solvents resulting in a second biocompatible material within the open network, said second biocompatible material having interconnected cavities, said interconnected cavities in the second biocompatible material allowing cells to grow functional tissues and allowing the diffusion of nutrients, metabolites and soluble factors throughout the scaffold.

Another aspect of the present invention relates to a method of making a three-dimensional biocompatible scaffold capable of supporting cell activities such as growth and differentiation, the method comprising providing a supporting grid comprising a first biocompatible material, said grid providing mechanical support of a second biocompatible material, said first material comprising one or more polymers, said grid forming an open network, adding a solution comprising a mixture of one or more biocompatible polymers and one or more solvents to a substantial part of the open network, removing said solvents resulting in a second biocompatible material within the open network, said second biocompatible material having interconnected cavities, said interconnected cavities in the second biocompatible material allowing cells to grow functional tissues and allowing the diffusion of nutrients, metabolites and soluble factors throughout the scaffold;

said grid further protecting the three-dimensional biocompatible scaffold against compressive forces during preparation, insertion and use.

Yet another aspect of the present invention relates to a three-dimensional biocompatible scaffold capable of supporting cell activities, such as growth and differentiation, the scaffold comprising a first and a second biocompatible material, said first material shaped as one or more grids of micro sized strands forming an open network of voids, said second material filling a substantial part of the voids of said open network, said second material being porous wherein the pores are interconnected, said second material having a plurality of open cells substantially uniformly distributed therein, said open cells being of an average size too small for the cells to infiltrate.

A preferred aspect of the present invention relates to a three-dimensional biocompatible scaffold capable of supporting cell activities, such as growth and differentiation, the scaffold comprising a first and a second biocompatible material, said first material shaped as one or more grids of micron sized strands forming an open network of voids, said second material filling a substantial part of the voids of said open network, said second material being porous wherein the pores are interconnected, said second material having a plurality of open cells substantially uniformly distributed therein, said open cells being of an average size too small for the cells to infiltrate, said grid providing protective mechanical support of the second biocompatible material, said grid further protecting the three-dimensional biocompatible scaffold against compressive forces during preparation, insertion and use, said second biocompatible material comprising one or more biocompatible polymers.

Figure 1:
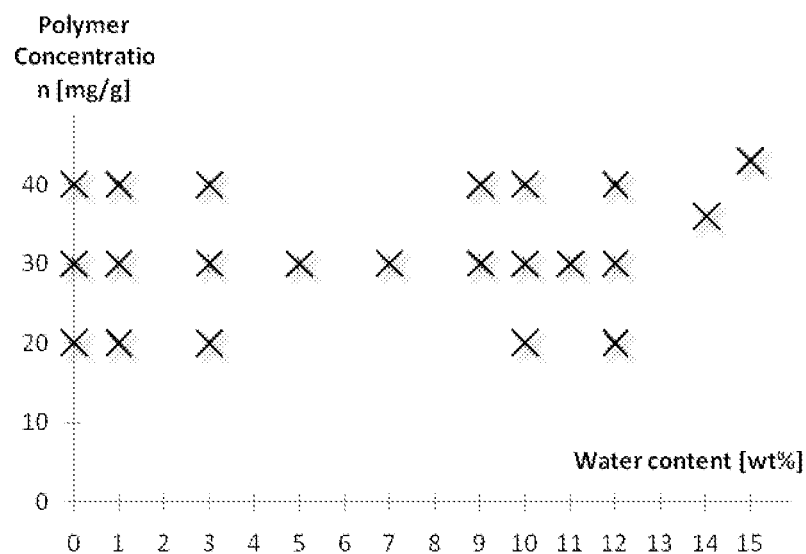
FIG. 1 shows the initial setup illustrated as the concentration of PCL in 1,4-dioxane as a function of the water content.

The present invention will now be described in more detail in the following.

DETAILED DESCRIPTION OF THE INVENTION

Definitions

Prior to discussing the present invention in further details, the following terms and conventions will first be defined:

Solid freeform fabrication (SFF) is a collection of techniques for manufacturing solid objects by the sequential delivery of energy and/or material to specified points in space to produce a solid. SFF is sometimes referred to as rapid prototyping, rapid manufacturing, layered manufacturing and additive fabrication.

Solvent Casting—Particulate Leaching (SCPL) allows the preparation of porous structures with regular porosity, but with a limited scaffold size. First the polymer is dissolved into a suitable organic solvent (e.g. polylactic acid could be dissolved into dichloromethane), and then the solution is cast into a mould filled with porogen particles. Such porogen can be an inorganic salt like sodium chloride, crystals of saccharose, gelatin spheres or paraffin spheres. The size of the porogen particles will affect the size of the scaffold pores, while the polymer to porogen ratio is directly correlated to the porosity of the final structure. After the polymer solution has been cast the solvent is allowed to fully evaporate, and then the composite structure in the mould is immersed in a bath of a liquid suitable for dissolving the porogen: water in case of sodium chloride, saccharose and gelatin or an aliphatic solvent like hexane for paraffin. Once the porogen has been fully dissolved a porous structure is obtained. Beside the small sized scaffold that can be obtained, another drawback of SCPL is the use of organic solvents which must be fully removed to avoid any possible damage to the cells seeded on the scaffold. Finally, it is the mould that determines the overall scaffold shape in contrary to SFF.

Gas foaming can be used to overcome the necessity of using organic solvents and solid porogens. This is done by using gas as the porogen. First disc shaped structures made of the desired polymer are prepared by means of compression moulding using a heated mould. The discs are then placed in a chamber where they are exposed to high pressure CO2 for several days. The pressure inside the chamber is gradually restored to atmospheric levels. During this procedure the pores are formed by the carbon dioxide molecules that abandon the polymer, resulting in a sponge like structure. A problem related to such a technique is caused by the excessive heat used during compression moulding. The excessive heat prohibits the incorporation of any temperature labile material into the polymer matrix. Secondly, large volume changes are accompanied with the pore formation making it difficult to control the final overall scaffold shape without using a mould. Again, introducing a restriction of the scaffold geometry is not present with SFF.

Emulsification combined with lyophilisation/freeze-drying is a technique that does not require the use of a solid porogen like SCPL. First a synthetic polymer is dissolved into a suitable solvent (e.g. polylactic acid in dichloromethane). Then water is added to the polymeric solution and the two liquids are mixed in order to obtain an emulsion. Before the two phases can separate, the emulsion is cast into a mould and quickly frozen by means of immersion into liquid nitrogen. The frozen emulsion is subsequently freeze-dried to remove the dispersed water and the solvent, thus leaving a solidified, porous polymeric structure. Freeze-drying allows a faster preparation as compared to SCPL, since it does not require a time consuming leaching step.

Thermally Induced Phase Separation (TIPS) is similar to the previous technique; this phase separation procedure requires the use of a solvent that can be solidified by lowering the temperature and which is easy to sublime. Dioxane could for example be used to dissolve polylactic acid. Phase separation is aided e.g. by the addition of a small quantity of water which results in the formation of a polymer-rich and a polymer-poor phase. During phase separation, the mixture is cooled below the solvent melting point and subsequently lyophilized to sublime the solvent, thereby obtaining a porous structure.

The term "biocompatible" is to be understood as, but not limited to, eliciting little or no immune response in a given organism. Indeed, since the immune response and repair functions in the body are highly complicated it is not adequate to describe the biocompatibility of a single material in relation to a single cell type or tissue.

The term "biodegradable" is to be understood as, but not limited to, the chemical, such as biochemical, breakdown of materials by a physiological environment, such as in a human or animal.

The term "open cells" is to be understood as, but not limited to, a delimited hollow space wherein the walls or surfaces are broken. It is not to be confused with the basic organizational unit of all living organisms. Hence, "open cells" is not a reference to living matter, e.g. cells isolated from living tissue.

The term "cavity" is to be understood as, but not limited to, both pores, interconnected pores, and "open cells". Unfortunately, within the engineering literature the words cavity and pores are referred to as "cells" and is not to be confused with the basic organizational unit of all living organisms.

The pH of blood is usually slightly basic with a value of pH 7.4. This value is referred to as physiological pH in biology and medicine.

The Scaffold

Polymeric scaffolds are intended to function as a temporary extracellular matrix (ECM) until regeneration of bone or other tissues has occurred. Therefore, the more closely it resembles an in vivo microenvironment, the more likely the success of the scaffold.

State-of-the-art polymeric scaffolding has been considered for the formation of 3D implant models that fit into specific defects. This is mainly obtained by fused deposition methods copying a 3D scanning image. Materials used are pure polymers, mixed polymers, or mixture of polymer and e.g. bone-conducting granules. But the precision deposition is restricted by the limited surface area available for cell attachments onto individual fibres.

Hence, in the present invention, a combination of the strict 3D structure with an interior providing abundant surface area for cell ingrowth is proposed as a new and reasonable solution. The abundant surface area is obtained by providing a material with a combination of submicrocellular structures and interconnected pores. Submicrocellular structures are defined as having an average cell size below about 1 micrometer.

Interconnectivity, the connection between the pores and/or the submicrocellular structures in the scaffold, is very important since it plays a decisive role in the diffusion of cells into the scaffold and the transport of nutrients and cellular waste products. The supermicrocellular structures are too small for the cells to infiltrate, and this allows for a constant and continuous transport of nutrients and cellular waste products within the whole scaffold. Without the supermicrocellular structures, the scaffold could risk clotting with infiltrating cells, resulting in a disruption of transport of nutrients and cellular waste products. This could result in disadvantageous cell death in the central regions of the scaffold.

One aspect of the present invention relates to a three-dimensional biocompatible scaffold capable of supporting cell activities, such as growth and differentiation, the scaffold comprising a first and a second biocompatible material, said first material shaped as one or more grids of micron sized strands forming an open network of voids, said second material filling a substantial part of the voids of said open network, said second material being porous wherein the pores are interconnected, said second material having a plurality of open cells substantially uniformly distributed therein, said open cells being of an average size too small for the cells to infiltrate.

In one embodiment of the present invention, the average size of said cells being from about 1 nanometer to about 6 micrometers, such as from about 1 nanometer to about 5 micrometers, such as from about 1 nanometer to about 4 micrometers, such as from about 1 nanometer to about 2 micrometers, such as from about 1 nanometer to about 1 micrometer, such as from about 1 nanometer to about 900 nanometers, such as from about 5 nanometers to about 800 nanometers, such as from about 10 nanometers to about 700 nanometers, such as from about 15 nanometers to about 600 nanometers, such as from about 15 nanometers to about 500 nanometers, such as from about 15 nanometers to about 300 nanometers, such as from about 20 nanometers to about 100 nanometers, preferably such as from about 25 nanometers to about 50 nanometers.

To guarantee good interconnectivity, the cell density of said cells in said second material in a preferred embodiment of the present invention is lying in a range from about $10^9$ (ten to the ninth power) to about $10^{20}$ cells per cubic centimeter of said second material, such as from about $11^{10}$ to about $10^{18}$, more preferably such as from about $12^{10}$ to about $10^{15}$ cells per cubic centimeter of said second material.

In another embodiment, the total volume of the cells in said second material comprise a fractional percentage of the total volume of said second material which lies within a range from about 10 to about 99 fraction percent, such as from about to about 98, such as from about 20 to about 95, more preferably such as from about 50 to about 90 fraction percent.

In even another embodiment, the average diameter of the pores in said second material being in a range of less than 1000 micrometers, such as within a range from about 0.01 to about 800 micrometers, such as within a range from about 0.1 to about 700 micrometers, such as within a range from about 1 to about 700 micrometers, such as within a range from about 1 to about 500 micrometers, such as within a range from about 10 to about 400 micrometers, preferably such as within a range from about 10 to about 50 micrometers.

The forces by which a single cell can pull are in the range of nPa and are phenotype specific Engler et al. (2006) studied the various cell reactions correlated to changes in the stiffness of a flat substrate and thereby demonstrating cell dependence on mechanical interaction. Specifically, he showed by microarray profiling, that substrate stiffness close to 1, 11, and 34 kPa can specify the lineage of a mesynchemal stem cell and commit it to respectively the phenotypes of neurons, muscle, or bone. Hence, it is possible to adjust the stiffness of the second biocompatible material of the present invention to the stem cell of interest.

Another aspect of the present invention relates to the use of the engineered scaffold for bone repair or regeneration, such as the engineered scaffold for use in the repair or regeneration of brain or spinal cord tissue.

Yet another aspect of the present invention relates to the use of the engineered scaffold for cartilage tissue repair or regeneration.

Yet another aspect of the present invention relates to the tissue engineering of complete or parts of organs (e.g. liver, kidney, and lung), such as the engineered scaffold for use in the treatment of liver diseases, kidney diseases, lung diseases, bone diseases, cartilage diseases or other tissue diseases.

Another aspect of the present invention relates to the use of the engineered scaffolds for the cultivation of cells and/or bacteria.

Yet another aspect of the present invention relates to the use of the engineered scaffold for soft tissue repair or regeneration.

Still another aspect of the present invention relates to the use of the engineered scaffold for brain or spinal cord tissue repair or regeneration.

Another aspect of the present invention relates to the use of the engineered scaffold for the manufacture of a medicament, such as the engineered scaffold for use as a medicament.

Another aspect of the present invention related to a method of implanting the scaffold of the present invention.

Yet another aspect of the present invention relates to the use of the engineered scaffold as a medicament.

Compressive Stiffness of Selected Tissues

The table below shows the compressive stiffness of selected tissues.

| Tissue: | GPa | Tissue | kPa |
| --- | --- | --- | --- |
| Cortical bone (human) | 4 | Brain | 3 |
| Trabecular bone (human) | 17 | Lens of the eye | 1.9 |
| Collagen | 1 | Liver | 275 |
|  |  | Articular cartilage | 800 |
|  |  | Meniscus | 100 |
|  |  | Elastin | 600 |
|  |  | Kidney | 45 |

Hence, to mimic the mechanical properties of a tissue, it may be contemplated that the scaffold must have equal compression stiffness as the tissue of interest to avoid collapsing under the local pressure provided by the body itself or by external forces. However, the stiffness of the scaffold must at the same time be adequate to direct the lineage of a mesynchemal stem cells to evolve into the correct tissue. It is seen from the work of Engler et al. (2006) that the optimal stiffness of a scaffold for generating bone tissue is 34 kPa. However, the compression stiffness of bone lies in the range of 4-17 GPa. Thus, the optimal stiffness of the scaffold may collapse under the local pressure provided by the body itself.

The inventors of the present invention have solved this problem by manufacturing a combined printed and freeze-dried scaffold.

Hence, a preferred aspect of the present invention relates to a three-dimensional biocompatible scaffold capable of supporting cell activities, such as growth and differentiation, the scaffold comprising a first and a second biocompatible material, said first material shaped as one or more grids of micron sized strands forming an open network of voids, said second material filling a substantial part of the voids of said open network, said second material being porous wherein the pores are interconnected, said second material having a plurality of open cells substantially uniformly distributed therein, said open cells being of an average size too small for the cells to infiltrate, said grid providing protective mechanical support of the second biocompatible material, said grid further protecting the three-dimensional biocompatible scaffold against compressive forces during preparation, insertion and use, said second biocompatible material comprising one or more biocompatible polymers.

The inventors of the present invention have made scaffolds wherein the compression stress (initial compressive stiffness) of the second biocompatible material of the three-dimensional biocompatible scaffold compression is in the range of 0.31-6.32 kPa. When combined with the supporting grid comprising a first biocompatible material, the compression stress was measured in the range of 360-5100 kPa. Mechanical tests on bulk specimens were carried out following ISO 3386-1.

In a preferred embodiment of the present invention, the compression stress of the supporting grid is 5 times higher than the second biocompatible material, such as in the range of 5-100000 times higher, e.g. 10 times higher, such as in the range of 15-90000 times higher, e.g. 50 times higher, such as in the range of 55-90000 times higher, e.g. 100 times higher, such as in the range of 200-50000 times higher, e.g. 500 times higher, such as in the range of 700-30000 times higher, e.g. 900 times higher, such as in the range of 1.500-20.000 times higher than the second biocompatible material.

In one embodiment of the present invention, the scaffold has a comparable value of compression stress to the value of compression stress of the targeted tissue. As an example, the inventors have produced a scaffold with a measured value of compression stress of 5100 kPa. Such a scaffold could be useful for trabecular bone reconstruction, where the trabecular bone has a value of compression stress of about 5000 kPa. A "comparable" value is to be understood as a value not deviating more than 35% from the other value, such as 25%, e.g. 20%, preferably not deviating more than 10%, e.g. 5%.

In another embodiment of the present invention, the scaffold has compatible compression strength to withstand the compressive pressure from the surrounding targeted tissue. "Compatible" compression strength is to be understood in such a way that the scaffold will remain substantially decompressed when the surrounding targeted tissue presses on the scaffold when implanted. The scaffold must not collapse during use. Substantially decompressed is to be understood in such a way that the scaffold volume must not be reduced more than 35% during use, such as 25%, e.g. 20%, preferably not more than 10%, e.g. 5%.

In one aspect of the present invention, cells having the capacity to differentiate into lineages of the desired tissue are seeded onto the scaffold. To improve the seeding efficiency, the scaffold may subsequently be coated with biocompatible polymers, thereby encapsulating the cells in the scaffold.

In one embodiment, the one or more biocompatible polymers in the second biocompatible material are negatively charged at physiological pH.

In another embodiment of the present invention, the one or more biocompatible polymers in the second biocompatible material are negatively charged at physiological pH. Furthermore, the scaffold comprises cells being seeded in vitro, the scaffold further comprising a first biocompatible polymer coating, said first biocompatible polymer coating comprising one or more biocompatible polymers being positively charged at physiological pH, said cells positioned in-between the second biocompatible material and the first biocompatible polymer coating.

In another embodiment, provided the first biocompatible polymer coating being positively charged, the scaffold further comprises a second biocompatible polymer coating, said second biocompatible polymer coating comprising one or more biocompatible polymers being negatively charged at physiological pH, said second biocompatible polymer coating positioned on top of the first biocompatible polymer coating.

In one embodiment, the one or more biocompatible polymers in the second biocompatible material are positively charged at physiological pH.

In another embodiment of the present invention, the one or more biocompatible polymers in the second biocompatible material are positively charged at physiological pH. Furthermore, the scaffold comprises cells being seeded in vitro, the scaffold further comprising a first biocompatible polymer coating, said first biocompatible polymer coating comprising one or more biocompatible polymers being negatively charged at physiological pH, said cells positioned in-between the second biocompatible material and the first biocompatible polymer coating.

In another embodiment, provided the first biocompatible polymer coating being negatively charged, the scaffold further comprises a second biocompatible polymer coating, said second biocompatible polymer coating comprising one or more biocompatible polymers being positively charged at physiological pH, said second biocompatible polymer coating positioned on top of the first biocompatible polymer coating.

In still another embodiment, the second biocompatible material is coated with a first biocompatible polymer coating comprising one or more biocompatible polymers being negatively charged at physiological pH and a second biocompatible polymer coating comprising one or more biocompatible polymers being positively charged at physiological pH. Furthermore, the scaffold comprises cells being seeded in vitro, said cells positioned in-between the first and second biocompatible polymer coatings.

In yet another embodiment, the second biocompatible material is coated with a first biocompatible polymer coating comprising one or more biocompatible polymers being positively charged at physiological pH and a second biocompatible polymer coating comprising one or more biocompatible polymers being negatively charged at physiological pH. Furthermore, the scaffold comprises cells being seeded in vitro, said cells positioned in-between the first and second biocompatible polymer coatings.

In another embodiment, the seeded cells have the capacity to differentiate into lineages of the desired tissue. In a preferred embodiment, the seeded cells may be of different type.

Another embodiment relates to a product produced/obtained by any of the above processes.

The Process

Throughout the recent years, an abundant number of processes has been suggested for the manufacturing of polymeric scaffolds, including solvent casting-particulate leaching, freeze-drying, rapid prototyping, electrospinning, and many more. Despite all the efforts, a specific method or combination of properties has not yet been shown to make significant difference, as long as the produced scaffolds hold some general properties, such as biocompatibility, high porosity, biodegradability, and clinical handle ability.

Many scaffold fabrication techniques are not capable of precisely controlling pore size, and pore geometry, or the formation of channels within the scaffold. When applying for approval for clinical use, this may be critical, because a clear description of the product is required. However, in the present invention, high uniformity is present in the developed scaffolds, because the micro- and nano-structures of the freeze-dried polymer are highly reproducible and steerable, and because the plotted backbone determines the outer shape. The size and shape of the final implant is a matter of computer aided design to print the wanted 3D template and adding the freeze-dried interior. The final scaffold can be understood as an open interconnected, hierarchically organised structure. At the micron to submicron length scale, the top/down manufacturing approach of rapid prototyping is used to make a structure that will constitute the frame into which the bottom/up processing approach of thermal induced phase separation form an open porous scaffold having a bimodal distribution of highly interconnected pores. One set of pores is above approximately 20 microns in size and the other set of pores or cells is below approximately 5 microns in size.

Thus, one aspect of the invention relates to a method of making a three-dimensional biocompatible scaffold capable of supporting cell activities such as growth and differentiation, the method comprising providing a supporting grid comprising a first biocompatible material, said grid providing mechanical support of a second biocompatible material, said first material comprising one or more polymers, said grid forming an open network, adding a solution comprising a mixture of one or more biodegradable polymers and one or more solvents to a substantial part of the open network, removing said solvents resulting in a second biocompatible material within the open network, said second biocompatible material having interconnected cavities, said interconnected cavities in the second biocompatible material allowing cells to grow functional tissues and allowing the diffusion of nutrients, metabolites and soluble factors throughout the scaffold.

Another aspect of the present invention relates to a method of making a three-dimensional biocompatible scaffold capable of supporting cell activities such as growth and differentiation, the method comprising providing a supporting grid comprising a first biocompatible material, said grid providing mechanical support of a second biocompatible material, said first material comprising one or more polymers, said grid forming an open network, adding a solution comprising a mixture of one or more biocompatible polymers and one or more solvents to a substantial part of the open network, removing said solvents resulting in a second biocompatible material within the open network, said second biocompatible material having interconnected cavities, said interconnected cavities in the second biocompatible material allowing cells to grow functional tissues and allowing the diffusion of nutrients, metabolites and soluble factors throughout the scaffold;

said grid further protecting the three-dimensional biocompatible scaffold against compressive forces during preparation, insertion and use.

In one embodiment, the one or more biocompatible polymers in the second biocompatible material are positively charged at physiological pH, and the process further comprises the following steps;

a) seeding the three-dimensional biocompatible scaffold obtained from claim 1 with cells,
b) coating the cell seeded scaffold with one or more biocompatible polymers being negatively charged at physiological pH, and
c) optionally, coating the cell seeded scaffold with one or more biocompatible polymers being positively charged at physiological pH.

In another embodiment, the one or more biocompatible polymers in the second biocompatible material are negatively charged at physiological pH, further comprising the following steps;

a) seeding the three-dimensional biocompatible scaffold obtained from claim 1 with cells,
b) coating the cell seeded scaffold with one or more biocompatible polymers being positively charged at physiological pH, and
c) optionally, coating the cell seeded scaffold with one or more biocompatible polymers being negatively charged at physiological pH.

In yet another embodiment, the method further comprises:

a) coating the scaffold surface with one or more biocompatible polymers being negatively charged at physiological pH;
b) optionally, seeding the scaffold with cells;
c) optionally, coating the scaffold surface with one or more biocompatible polymers being positively charged at physiological pH.

In one embodiment, the method further comprises:

a) coating the scaffold surface with one or more biocompatible polymers being positively charged at physiological pH;
b) optionally, seeding the scaffold with cells;
c) optionally, coating the scaffold surface with one or more biocompatible polymers being negatively charged at physiological pH.

In still another embodiment, said mixture comprises two or more solvents.

In another embodiment, the seeded cells have the capacity to differentiate into lineages of the desired tissue. In a preferred embodiment, the seeded cells may be of different type.

Diffusion throughout the scaffold is to be understood in the meaning, but not limited to, that substantially the entire scaffold is diffused, such as for example about 99%, such as about 90%, such as about 80%, such as about 70% of the scaffold is diffused. Transport mechanisms (diffusion and convection) can be guided through larger channels with in the scaffold.

The term "scaffold" is to be understood as, but not limited to, the construct ready for implantation, e.g. suitable for use as an implant. In certain aspects of the invention, the scaffold is cut before implantation to fit the defect.

The size of the scaffold must reflect the defect size, but also the migration rate of cells, e.g. within the scaffold, should be taken into account. When no printed backbone was present and a high cell density ($3.5 \times 10^6$/scaffold) was used, the most openly structured interior of the scaffolds (0.07) had homogenous cell distribution throughout their full height of approximately 5 mm and therefore cell migration therein must be considered favourable. A lower concentration of PCL may enhance this even further, and therefore 20 mg/g is currently evaluated for use in the combined scaffolds. The print of the scaffold backbone/grid should be sufficiently openly structured for the freeze-dried material to obtain full porosity—thereby ensuring good migration and mass transport.

High porosity is obtained by the two solvent thermal induced phase separation, but the mechanical properties were inversely proportional to porosity. Therefore, a stabilising backbone/grid was incorporated into the highly porous scaffolds in the form of a printed scaffold. By this manufacturing combination, an outermost stable scaffold possessing a flexible interior for cell adhesion and migration was made. This may be advantageous when scaffolds are to be used for transplantation, because completely flexible scaffolds could hold issues in remaining fitted into a specific defect during time.

Another aspect of the invention relates to a method, wherein the interconnected cavities are formed by thermal induced phase separation and/or lyophilisation of the solvents.

Yet another aspect of the invention relates to a method, wherein the cavities are formed by gas foaming.

Another aspect of the invention relates to a method, wherein the cavities are formed by salt leaching and thermally induced phase separation.

Still another aspect of the invention relates to a method, wherein the grid is made by solid freeform fabrication.

Yet another aspect of the invention relates to a method, wherein the average pore size of the second biocompatible material is in the interval of 0.01 to about 800 micrometers, such as within a range from about 0.1 to about 700 micrometers, such as within a range from about 1 to about 700 micrometers, such as within a range from about 1 to about 500 micrometers, such as within a range from about 10 to about 400 micrometers, preferably such as within a range from about 10 to about 50 micrometers.

Another aspect of the invention relates to a method, wherein the mixture comprises at least two solvents, such as within a range from about 3 to about 10 solvents, such as within a range from about 3 to about 5 solvents.

Non-limiting examples of solvents are hexane, heptane, benzene, carbon tetrachloride, chloroform, acetic acid, ethyl acetate, THF, methylene chloride, acetone, ethanol, methanol, propanol, isopropanol, dioxane, acetonitrile, dimethylformamide, DMSO and water.

Still another aspect of the invention relates to a method, wherein the freezing points of the solvents are separated from each other by at least 5 degree Celsius, such as within a range from about 5 to about 100 degree Celsius, such as within a range from about 6 to about 95 degree Celsius, such as within a range from about 8 to about 90 degree Celsius, such as within a range from about 10 to about 70 degree Celsius, preferably such as within a range from about 5 to about 100 degree Celsius.

Yet another aspect of the invention relates to a method, wherein the scaffold surface is coated with a natural or synthetic coating material such as protein, peptides, nucleotides, and/or small interfering RNAs.

In yet another aspect, the invention relates to an engineered tissue made by contacting the biocompatible active three-dimensional scaffold made by the previously described method with cells in vivo or in vitro under conditions effective to allow interaction between the biocompatible three-dimensional scaffold and the cells. In certain embodiments, the cells are members selected from the group consisting of stem cells, progenitor cells, and/or differentiated cells, e.g. partially or fully differentiated cells. In another embodiment, the cells are members selected from the group consisting of regenerative cells. In certain embodiments, the cells are at least one of neural cells, epithelial cells, cardiac myocytes, pulmonary lung cells, keratinocytes, and endothelial cells. In certain embodiments, the cells are PC12 or neuronal-restricted precursor (NRP) cells and the engineered tissue is a neurone producing tissue.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

In one aspect of the present invention, the scaffold of the present invention may be replicated by two-photon polymerization, the principle disclosed in a paper by Andreas Ostendorf et al.

EXAMPLES

Manufacturing of Printed and Freeze-dried Scaffolds
Scaffolds—Freeze-dried

Scaffolds were manufactured by thermal induced phase separation (TIPS) followed by freeze-drying of polycaprolactone (PCL, commercial grade 6405, Solvay). Briefly, PCL was dissolved in 1,4-dioxane at room temperature. When a homogenous mixture was obtained, a small amount of water was added. The scaffold preparation was carried out in a laminar flow bench, and the setup is seen in FIG. 1. Three types of scaffolds were biologically tested and denoted e.g. 0.01, 0.03, and 0.07 in accordance with their water content in percent. The polymer concentration was 20, 30 or 40 mg PCL/g dioxane.

The mixture was cast into glass cylinders (diameter=9.6 mm, at room temperature). Cylinders were transferred into a freeze-drier and temperature lowered (2.5° C./min) to −25° C. for 20 hours. Because solidification temperature is 12° C. for 1,4-dioxane and 0° C. for water, crystals form at different time points. This process ends up in complete solidification of the mixture leaving the PCL chains packed between crystal boundaries. The temperature was increased to −5° C. and pressure lowered to ~50 mTorr before freeze-drying was applied, and sublimation (i.e. direct solid to gaseous phase shift) initiated. PCL cylinders were frozen in liquid nitrogen before being cut into final scaffold size by a razorblade. Height was 5-10 mm for in vitro and 2 mm for in vivo studies. Scaffolds were sterilised through graded series of ethanol (96%, 70%, 50%; intervals of 30 min) and washed in sterile water afterwards. To enhance scaffold hydrophilicity, the surface was etched with 1.25 M NaOH for 16 h (produces COO$^-$ groups) and neutralised with 1 M HCL for 1 h (protonates COO$^-$ groupsto COOH), followed by extensive rinsing in sterile water. Scaffolds were dried or stored cold in saline until use.

Scaffolds—3D Printed

A rapid prototyping apparatus, Bioscaffolder (SysEng, Hünxe, Germany) was used to print PCL scaffolds. The PCL polymers (T=108° C.) were extruded from a needle of 200 μm in diameter (final fibre diameter ~175 μm) and deposited layer-by-layer in accordance with a model loaded into the Bioplotter CAM software. The deposition speed was 240 mm/min and distances between fibres were ~600 μm (0/90 degree pattern) to allow for a high porosity. The scaffolds were cylinder-shaped (10 mm diameter×5 mm height).

Cells and Culturing of Constructs

The cells used for testing the PCL scaffolds were hMSC-TERT seeded and cultured in basic medium or in basic medium supplemented by 100 nM dexamethasone, 290 nM ascorbic acid (Merck, Darmstadt, Germany) and 5 mM β-glycerophosphate for mineralisation assays (osteogenic media). Density of seeding varied from 1-3.5×10$^6$ cells per scaffold.

Cellularity of Constructs

Freeze-dried scaffolds of 5 mm height was seeded with 2×106 cells, and cultured for up to 21 days in basic medium as described previously. DNA amounts were determined by PicoGreen according to manufacturer's instructions (n=4).

Transplantation into Mice

To determine in vivo cell ingrowth and degradation behaviour, non-seeded 0.01 and 0.07 scaffolds were transplanted into male CDF1 mice (18-20 weeks old, 25-45 g). Operations were performed under anaesthesia (25 mg/kg Fluansione, 0.7875 mg/kg Fentanyl Citrate, and 12.5 mg/kg diazepam, i.p.). Mice skin was disinfected with 70% ethanol prior to surgery. A one centimeter skin incision was made on the dorsal side of each mouse, and two subcutaneous pouches formed by blunt dissection. One scaffold was placed in each pouch, and scaffold order randomised regarding side and mouse. Both scaffold types were present in 4 replicates. Incisions were closed with sutures, and mice treated for three postoperative days with analgesia (5 mg/kg Carprofen, s.c.). After 1-6 weeks of implantation, mice were euthanized using Pentobarbital i.p., and samples were retrieved for histological analysis. All animal experiments were approved by the Danish Institutional Animal Care and Use Committee.

Live/Dead Staining

Viability tests were performed using the live/dead staining kit in accordance with manufacturer's instructions.

Histology

For histological analysis, both the in vitro and in vivo samples were fixed in 4% formaldehyde solution (pH 7.0), embedded in Technovit® 7100 (Ax-lab, Vedbk, Denmark), and cut in 10 µm sections using a Polycut E microtome (Reichert & Jung, Heidelberg, Germany). Sections were taken from the central part of the scaffold and stained with haematoxylin and eosin. Images were acquired on a BX50 microscope using a Camedia C-5060 digital camera (Olympus, Denmark). Other in vitro sections were stained by Goldner's trichrome staining. This method consists of staining in 0.4% acidic fuchsin (5 min), orange G (20 min), and 2% light green (5 min) with acetic acid rinses between all steps. Sections were counterstained with Haematoxylin in distilled water. The nuclear chromatin stains blue, mineralised bone green, and collagen/osteoid bright red.

Actin Immunostaining

Cytoskeletal arrangement was determined by actin staining. Constructs cultured for 24 h were fixed in 4% paraformaldehyde in PBS, and stained using the actin cytoskeleton and focal adhesion staining kit (Chemicon International, Inc.) according to manufacturer's instructions. TRITC-conjugated phalloidin dilution was 1:400 (incubation time 60 min at room temperature, actin staining), and DAPI 1:1000 (incubation time 5 min, nucleic counterstaining). Images were acquired on laser scanning microscope 510 Meta. Laser excitation was 543 nm, and emission filter transmitted light between 520/554 and 580 nm for actin visualisation.

SEM

For SEM, the scaffolds were centrally cut with a razorblade after freezing in liquid nitrogen and the constructs were fixed in 2.5% glutaraldehyde containing 0.1 M sodium cacodylate buffer (pH 7.4) and dehydrated in a graded series of ethanol (50, 70, 90, 99%; intervals of 30 min) before being transferred to exicator for air drying. Scaffolds and constructs were analysed using a low vacuum secondary electron detector (Nova NanoSEM 600, FEI Company).

High Resolution X-ray Tomography

The X-ray tomographic microscopy (XTM) studies were carried out at the experimental station ID19 of the European Synchrotron Radiation Facility (Grenoble, France) taking advantage of the high contrast acquired due to the high intensity of the X-ray source realized by the synchrotron. A wiggler was used to select 20-keV photons and by the detection device used, visible light were produced by an X-ray-sensitive converter and imaged onto a cooled charge-coupled device in a FReLoN camera. The end resolution was governed by the beam characteristics and the effective pixel size of the detector selected to be 0.28 µm with a field of view of 0.6×0.6 mm$^2$. The data set from a single sample comprised an angular scan of 1500 images obtained during rotation of the specimen in steps of 0.12° at a sample-to-detector distance of 8 mm. The exposure time was 0.15 s per picture. This image acquisition protocol is followed by a calculation of the spatial distribution of matter reconstructed from the projection images using the parallel beam filtered back-projection algorithm implemented in the ESRF software PyHST. This provides a 3D image comprising voxels having grayscale values from 0 to 255. From this image a rendering of the material morphology can be visualized as isosurfaces by interpolating a surface between equi-valued voxels. A single voxel within this image have the dimensions of 280×280×280 nm. Thus, slices through this 3D image can reveal the morphology of the analyzed scaffold. Samples of approximately 8 mm$^3$ were analyzed (n=2). They were mounted on the surface of an aluminum cylinder with cyanoacrylate glue, and the cylinder was placed on a rotation stages within the tomography station.

Polycaprolactone Scaffolds

Figure 2:
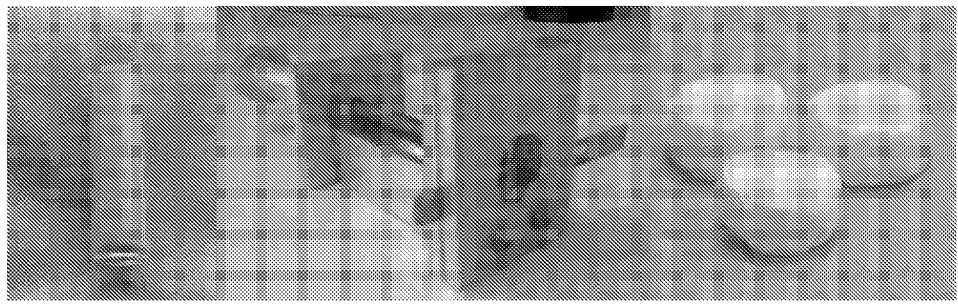
FIG. 2 shows a freeze-dried scaffold in glass cylinder, "Guillotine" for cutting scaffolds, and final scaffold samples of 10 mm diameter×5 mm height.

The freeze-drying of PCL in glass tubes resulted in long cylinders of scaffolds (FIG. 2). They were cut manually in a "guillotine" so the final scaffolds varied slightly in height. A pyrolysis mass spectrometry was carried out and showed no residual organic solvent in the scaffolds regardless of the water content.

Figure 3:
FIG. 3 shows the angle contact measurement before (left) and after (right) NaOH-treatment. Surface hydrophilicity is significantly enhanced after treatment.

Freeze-drying resulted in a very hydrophobic surface regardless of water content. As visualised by contact angle measurement (FIG. 3), the angle decreased steeply after NaOH treatment indicating that the surface became significantly more hydrophilic.

Figure 4:
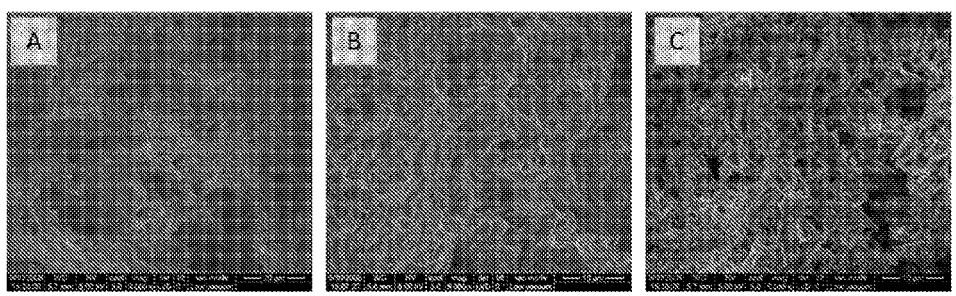
FIG. 4 shows SEM images of 1 wt % of H2O (A), 3 wt % of H2O (B), and 7 wt % of H2O (C) scaffolds. More heterogeneous surface patterns were observed with increasing water content.
Figure 5:
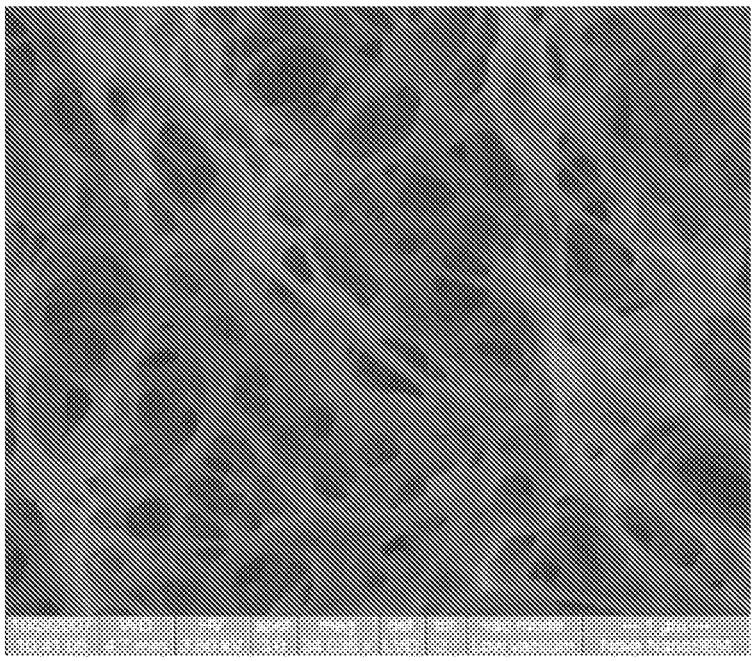
FIG. 5 shows a high resolution SEM image of nanostructures within the scaffolds made from solution with 7 wt % of H2O. The smallest features are down to 10 nm. This morphology is consistent through the scaffolds.

SEM revealed some structural differences with 0.01 scaffolds tending to be more homogenously surfaced than 0.07 and 0.03 (FIG. 4). The 0.07 scaffolds had a very rough surface pattern with lots of cracks and struts, whereas the 0.01 were smoother in appearance. These appearances were reproducible between several manufactured batches. When looking closely at 0.07 scaffolds, a homogenous, fine ECM-like structure was revealed (FIG. 5) that closely mimicked the various fibre sizes of natural tissue.

Figure 6:
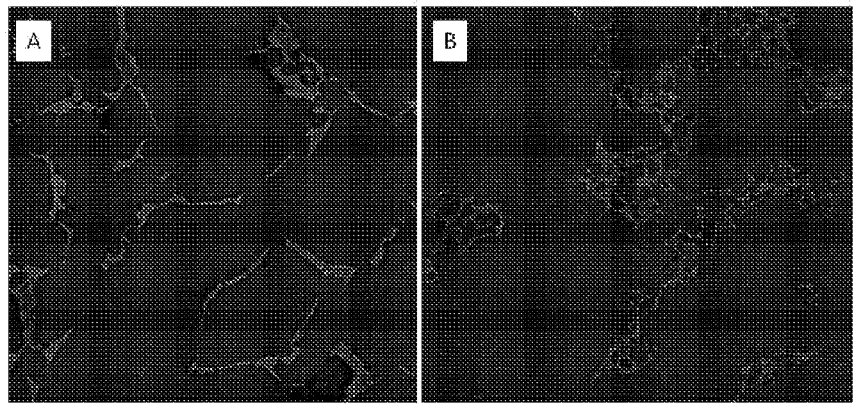
FIG. 6 shows Nanotomography images from ESRF. Scaffolds shown are solid walled made from solutions with 1 wt % of H2O (A) and porous walled made from solutions with 7 wt % of H2O (B). Walls in (A) are ~5 µm wide and both images are at the same length scale.
Figure 7:
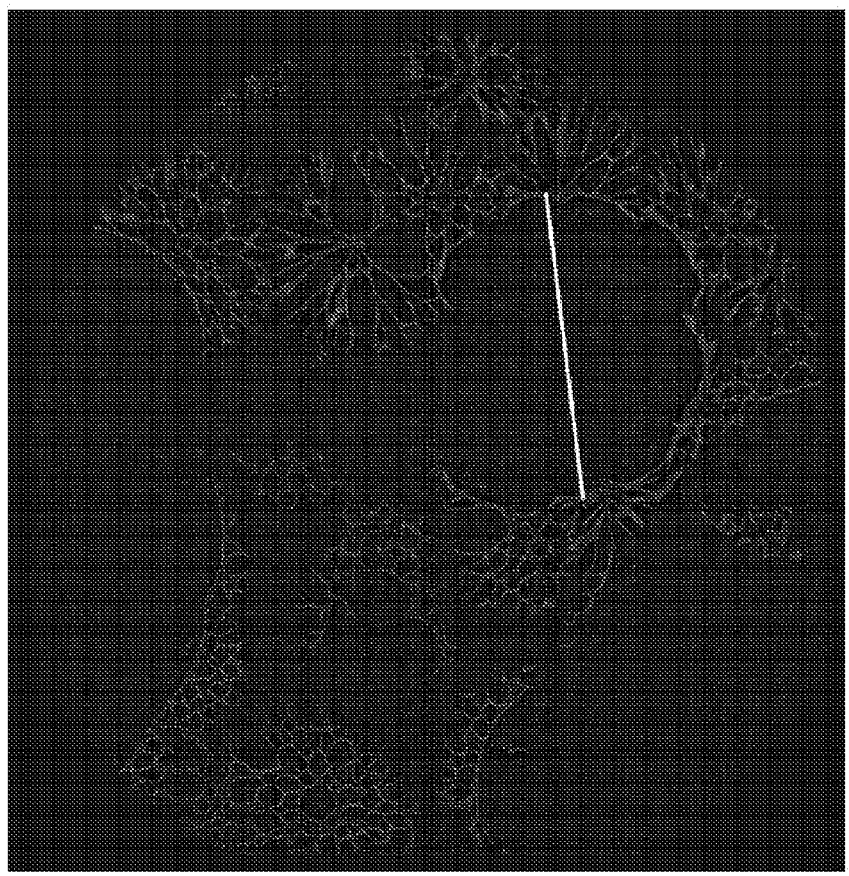
FIG. 7 shows a Nanotomography image from ESRF. The double graded scaffold is made from solution containing 7 wt % of H2O. The scale of this image is equivalent to the scale of the images in FIG. 6. Large pore diameter (white line) is 175 µm, while the smaller ones are ~10 µm.

High resolution microtomography showed a double graded scaffold structure (FIG. 6) depending on the amount of water added during the preparation due to the different crystallisation points of the two solvents. Scaffolds consisted of regular larger pores of approximately 250 µm with various amounts of porosity in the pore walls (ranging from 0 in 0.01 scaffolds to sizes up to 1-5 µm in 0.07 scaffolds). Increasing amounts of water resulted in a significantly increased surface area for cell attachment. This double porosity was formed by water crystals (small pores) trapped in the polymer solution after crystallisation of dioxane (larger pores) and a certain amount of >5-6% water was required, as no porous pore walls was formed with 1 or 3% water content. For 0.01 scaffolds with lower concentration of polymer (30 mg/g), the resultant scaffolds had thinner walls, but similarly sized pores and no double grading (Data not shown). When a larger section of the 0.07 scaffold was visualised, a flower-like structure was seen (FIG. 7). The entrapped water crystals in the pore walls may have caused an explosion-like conversion when sublimating, as many of the walls seems inside out pointing (see for example the fan-like area just above the upper end of the white line).

Figure 8:
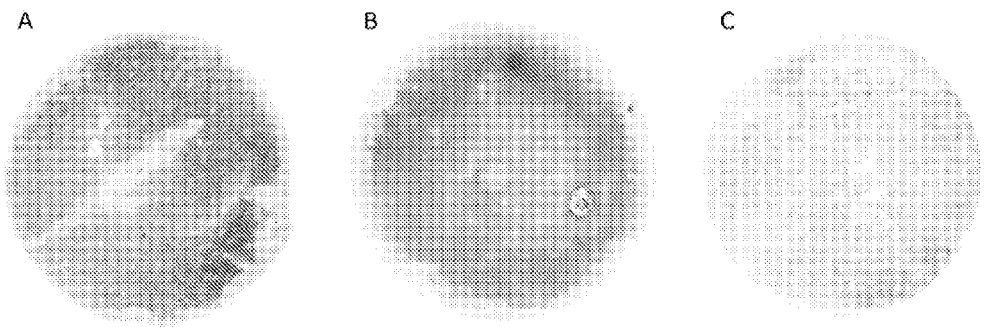
FIG. 8 shows live/dead staining of $1 \times 10^6$ hMSC-TERT on scaffolds made from solutions with 1 wt % H2O (A), 3 wt % H2O (B), and 7 wt % H2O (C) scaffolds. More superficially located cells were observed on (A) and (B) scaffolds as compared with (C)

In live/dead staining (FIG. 8), the intensity gradient from 0.01 towards 0.07 may have reflected the high superficial number of cells in the 0.01 as compared to the more regularly dispersed cells in 0.07. In general, the cell seeding patterns on the surfaces closely reflect the wavy nature of the scaffold surfaces, resulting in heterogeneous appearances of cell layers.

Figure 9:
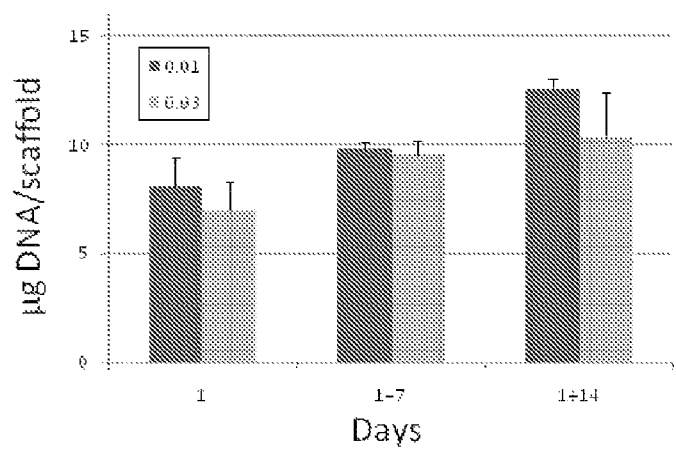
FIG. 9 shows DNA quantification of hMSC-TERT on 1, 8, and 15 days of culture. The amount of DNA is expressed as mean±SD (n=4). Seeding was $2 \times 10^6$ hMSC-TERT/scaffold.

The cellularity of PCL scaffolds was estimated from DNA quantification. A large amount of the 0.07 scaffolds dissolved during sterilisation, and hence the number needed for a reliable DNA quantification (n=4/time point) was not obtained. Therefore, only the results from 0.01 and 0.03 are presented (FIG. 9). The cellularity was slightly higher in the 0.01 scaffolds at all time points, but no obvious differences were found. The small increase in cellularity during culture indicated that proliferation was not optimal, presumably because cell grew merely at the surface of scaffolds (see histology-images FIG. 11)

Figure 10:
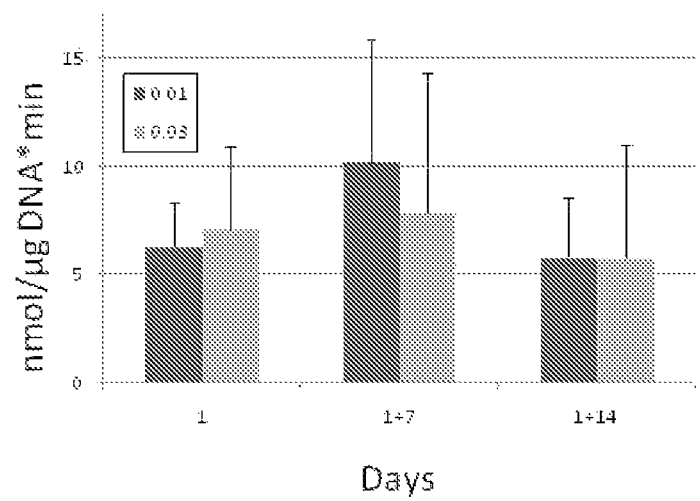
FIG. 10 shows activity of the alkaline phosphatase (ALP) enzyme on 1, 8, and days of culture. The activity is expressed as mean±SD (n=4). Activity is indicated in nanomole p-nitrophenol/microgram DNA per minute (nmol/µg DNA* min). Seeding was $2 \times 10^6$ hMSC-TERT/scaffold.

Regarding the ALP enzyme activity, peak levels were obtained after 8 days for both scaffold types (FIG. 10).

Figure 11:
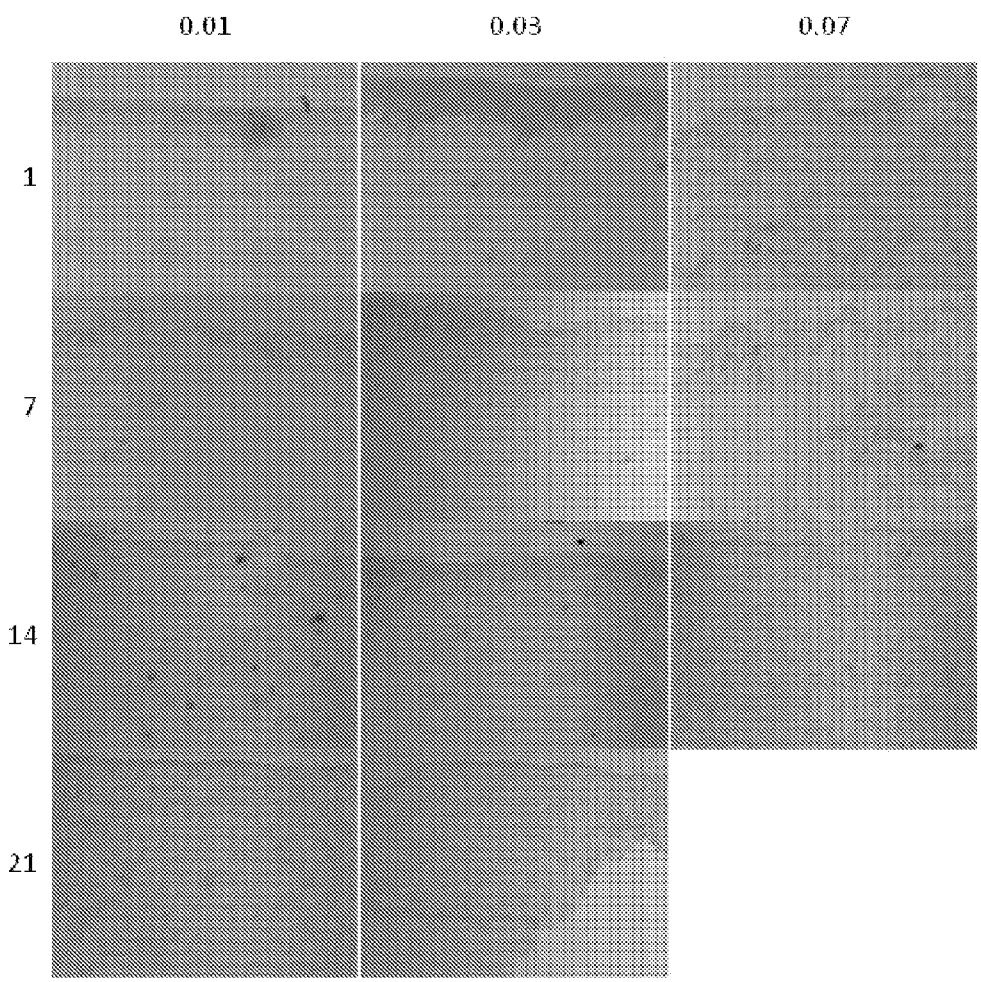
FIG. 11 shows H&E staining of histological sections after up to 21 days of in vitro culture. Seeding was $3.5 \times 10^6$ hMSC-TERT/scaffold. Homogenous distribution of hMSC-TERT was observed in 7 wt % H2O scaffolds from day 1, but not until day 15 in 3 wt % H2O and day 21 in 1 wt % H2O scaffolds.
Figure 12:
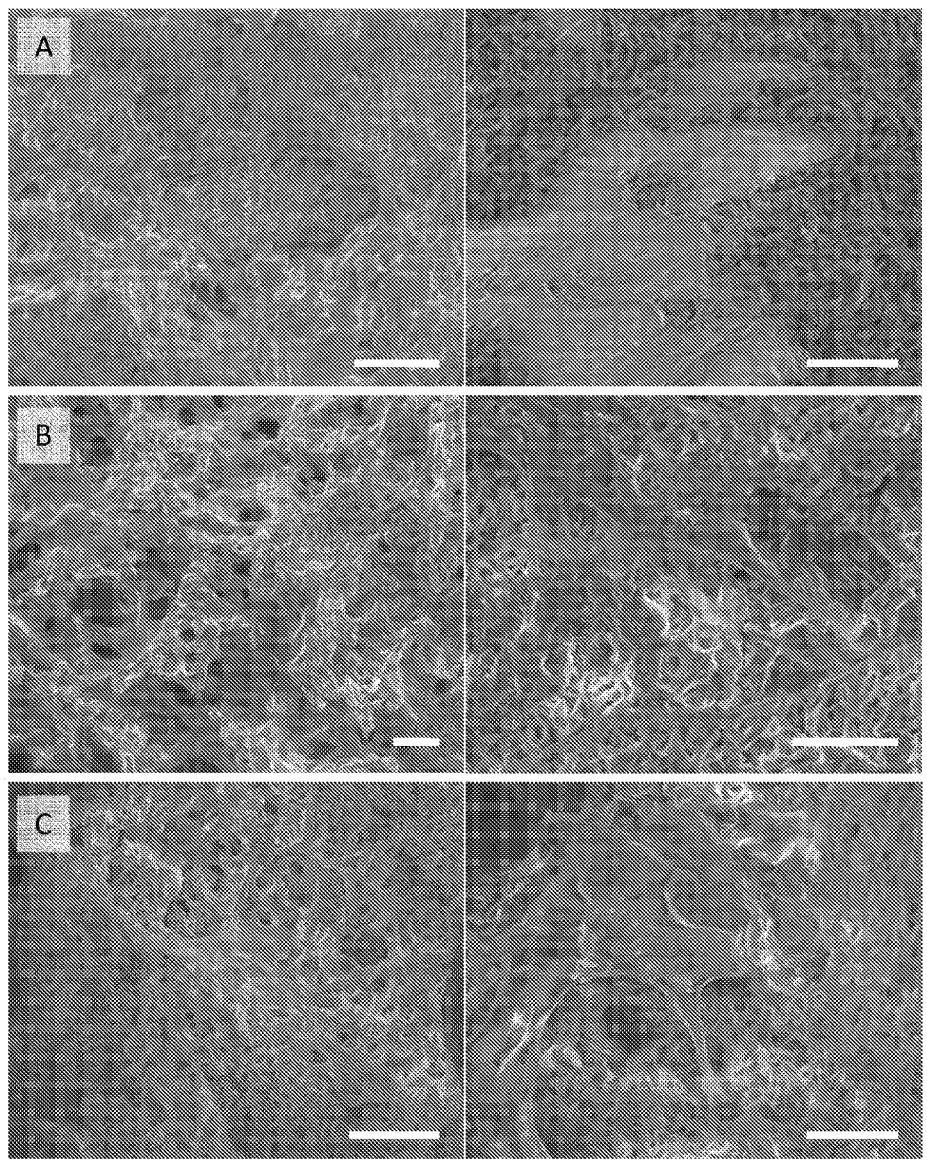
FIG. 12 shows SEM images of cellular adhesion to the various scaffolds. Cells adhered closely to the type 1 wt % H2O scaffolds (A) and the type 3 wt % H2O scaffolds (B) surfaces, but more superficially to the type 7 wt % H2O scaffolds (C). Bars represent 20 µm in the left column and 10 µm in the right.

The ingrowth of cells was considerably different in the three scaffold types (FIG. 11). The 0.01 and 0.03 scaffolds had a superficial cell layer on days 1 and 7, whereas the 0.07 scaffolds had a homogenous distribution of cells throughout the entire cross section already from day one. Homogenous distribution of cells in scaffolds was not achieved until day 21 for the 0.01 scaffolds and day 14 for the 0.03 scaffolds. The 0.07 scaffolds were the first scaffold observed (including ceramic ones) to have completely homogenous cellular distribution on day 1. Cells adhered to all three scaffold types (FIG. 12). On 0.01 scaffolds, the cells were smooth and placed in close proximity of scaffolds structures, spanning only few smaller grooves in the surface. The stretched appearance was more pronounced in the 0.03 scaffolds, but most noticeable in the 0.07 scaffolds, where a high number of grooves were spanned by stretched out cells holding many adhesion points. On the 0.07 scaffolds, cells tended to have a floating appearance touching only the tip of the scaffold structures—this was not verified on the histology sections.

Figure 13:
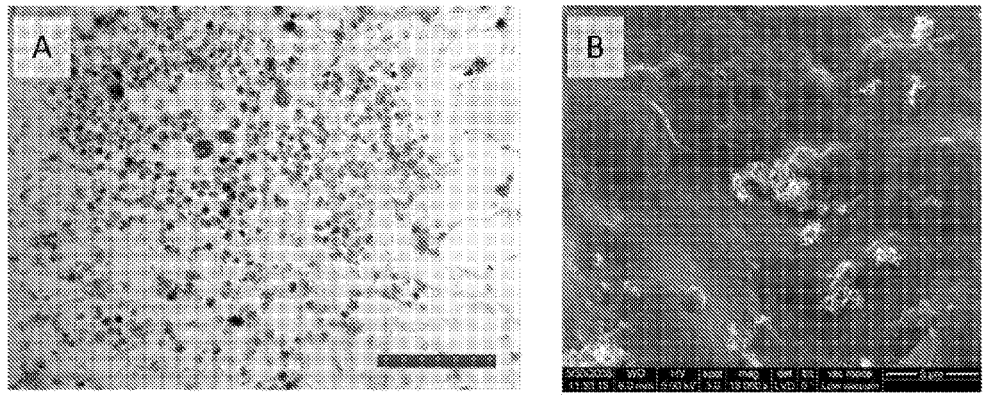
FIG. 13 shows Goldner's trichrome staining (A) and SEM (B) image of scaffolds. Mineralisation of hMSC-TERT was observed after 21 days of culture in all scaffold types, and images are representative for type 1-7 wt % of H2O scaffolds. Mineralised cells and nodules on surfaces were observed (bars are A: 150 µm and B: 5 µm)

After three weeks of culture in osteogenic medium, areas of mineralised cells formed as visualised by trichrome staining of histological sections (FIG. 13). The various differentiation levels was recognised in the staining; Pale green cells were mineralising osteoblasts, rounded red cells were non-mineralised pre-osteoblasts, and elongated light red cells were non-differentiated precursor cells. SEM showed formation of small (0.5-1 µm) nodule-like structures in clusters on the surface of constructs. Images are representative for the three scaffold types.

Figure 14:
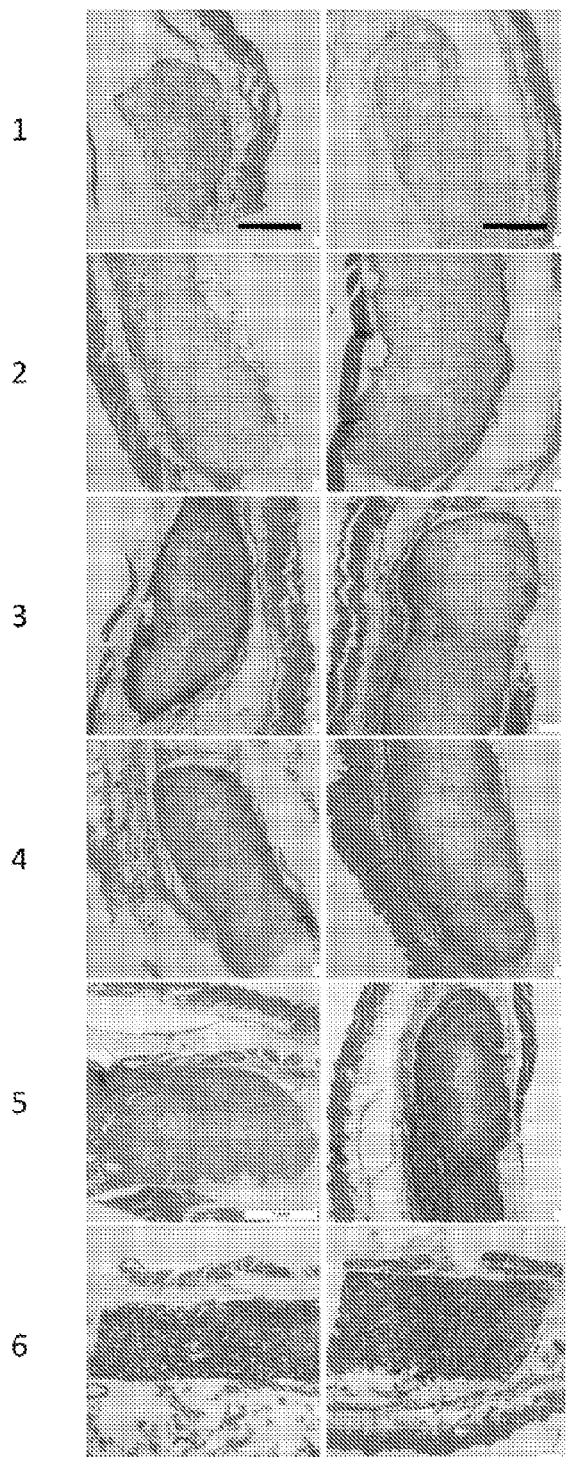
FIG. 14 shows type 1 wt % H2O scaffolds of 2 mm height implanted subcutaneously in mice. The numbers on the left refer to the number of weeks in the mice (Bar=1 mm)
Figure 15:
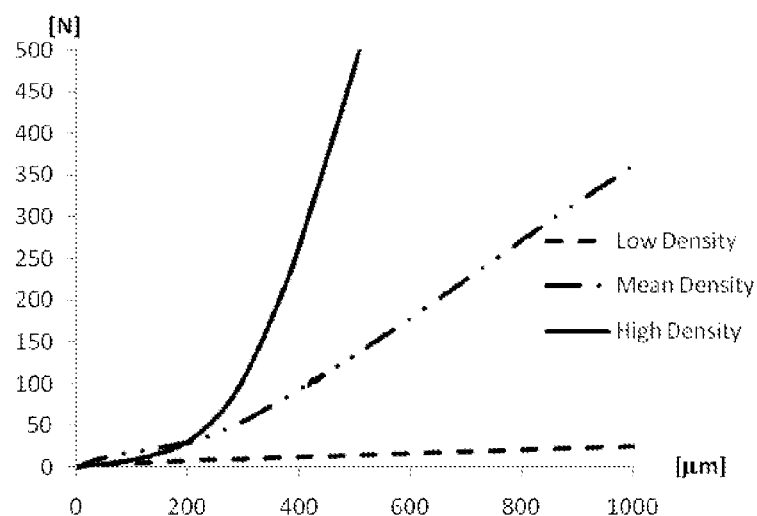
FIG. 15 shows a compression test. Low, mean, and high density is denominating 20, 30, and 40 mg/g polymer-solution.

Empty scaffolds were subcutaneously implanted in mice, and during the experiment no inflammatory signs or adverse tissue reactions were observed. Ingrowth of recipient's cells was observed from week one, but not until week four was a fully cellularised scaffold obtained (FIG. 14). During the observation period, more and more matrix formation and shrinkage of the scaffolds were identified. After six weeks, the scaffolds were completely infiltrated with cells, but not profoundly degraded. Few multinucleated cells associated with inflammatory response were observed in six weeks sections, indicating biocompatibility between host tissue and PCL.

A general problem arose with the mechanical properties of these scaffolds. Very low stability was obtained, and disintegration during "guillotine" cutting and NaOH preparation was regularly observed. Compression test revealed that porosity and rigidity was inversely proportional—estimated rigidity was 0.31, 5.76, and 6.32 kPa for 0.01, 0.03, and 0.07, respectively.

Figure 16:
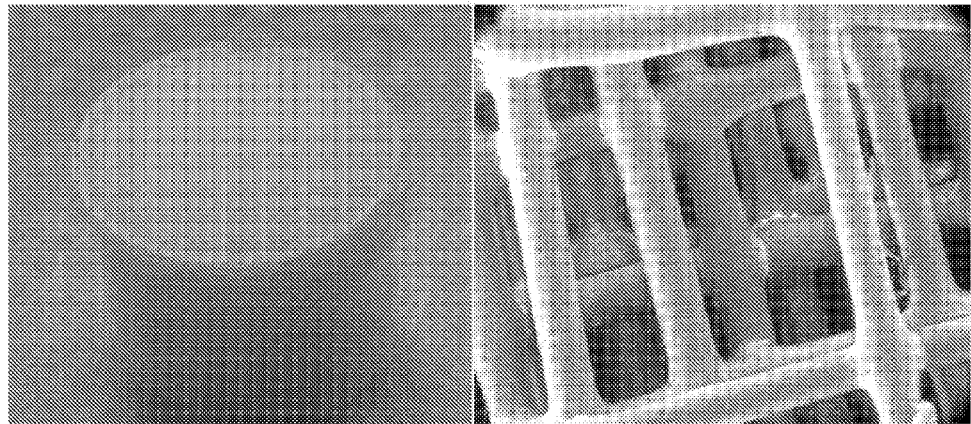
FIG. 16 shows a 3D plotted scaffold 10 mm diameter×10 mm height. SEM image shows the highly porous microstructure of scaffolds with solid fibres of ~175 µm diameter.
Figure 17:
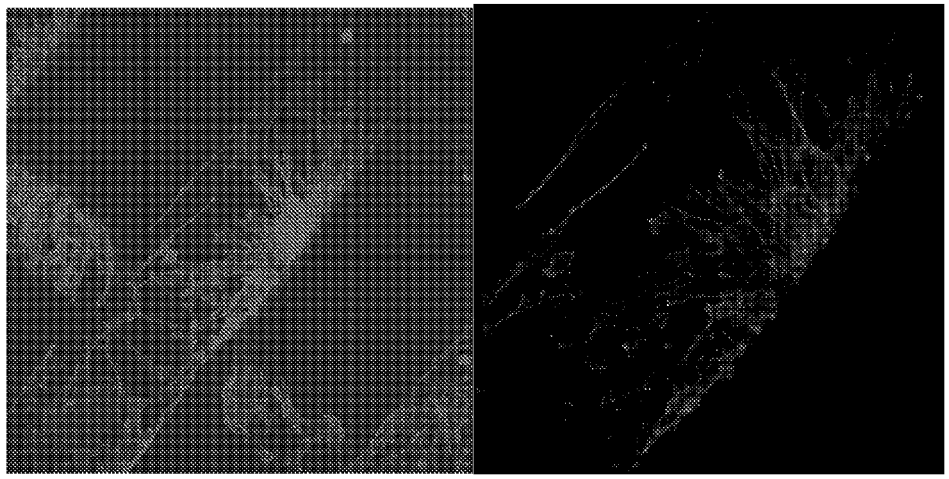
FIG. 17 shows Actin and Hoechst staining of cells on plotted scaffolds after initial adhesion for 24 h. Diameter of one fibre is ~175 μm.

To optimise the mechanical properties of scaffolds, another manufacturing method was tried out; rapid prototyping or 3D printing. 3D printing resulted in very homogeneous scaffolds of defined structure and porosity (FIG. 16). Layers are deposited on top of each other, and because the polymer solution is melted when printed, the individual fibres are fastened to the subjacent ones—resulting in good stability of the many layers. The mechanical properties were profoundly enhanced as compared to freeze-dried scaffolds as each fibre was solid. Actin filaments are highly involved in cell attachment and migration, and staining thereof was used to illustrate biocompatibility between the hMSC-TERT cells and printed scaffolds (FIG. 17). An abundant number of adhesion points were indicated by the actin stretching out on the surfaces, and was taken as an indicator for biocompatibility between scaffolds and cells after the melt deposition manufacturing. But the high porosity of scaffold walls from the freeze-dried scaffolds was lost, and therefore confluence on the scaffolds was obtained at a much lower cell density.

Figure 18:
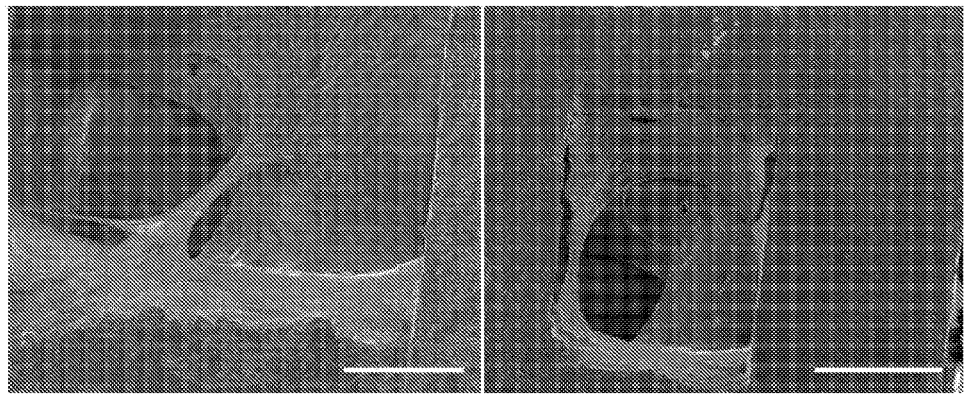
FIG. 18 shows SEM images of cells on plotted scaffolds after initial adhesion for 24 h. Bar represents 100 μm (left) and 200 μm (right)

In accordance with actin staining, SEM revealed good adhesion of cells to printed scaffolds, and cells stretching between the various layers of the scaffolds (FIG. 18).

Figure 19:
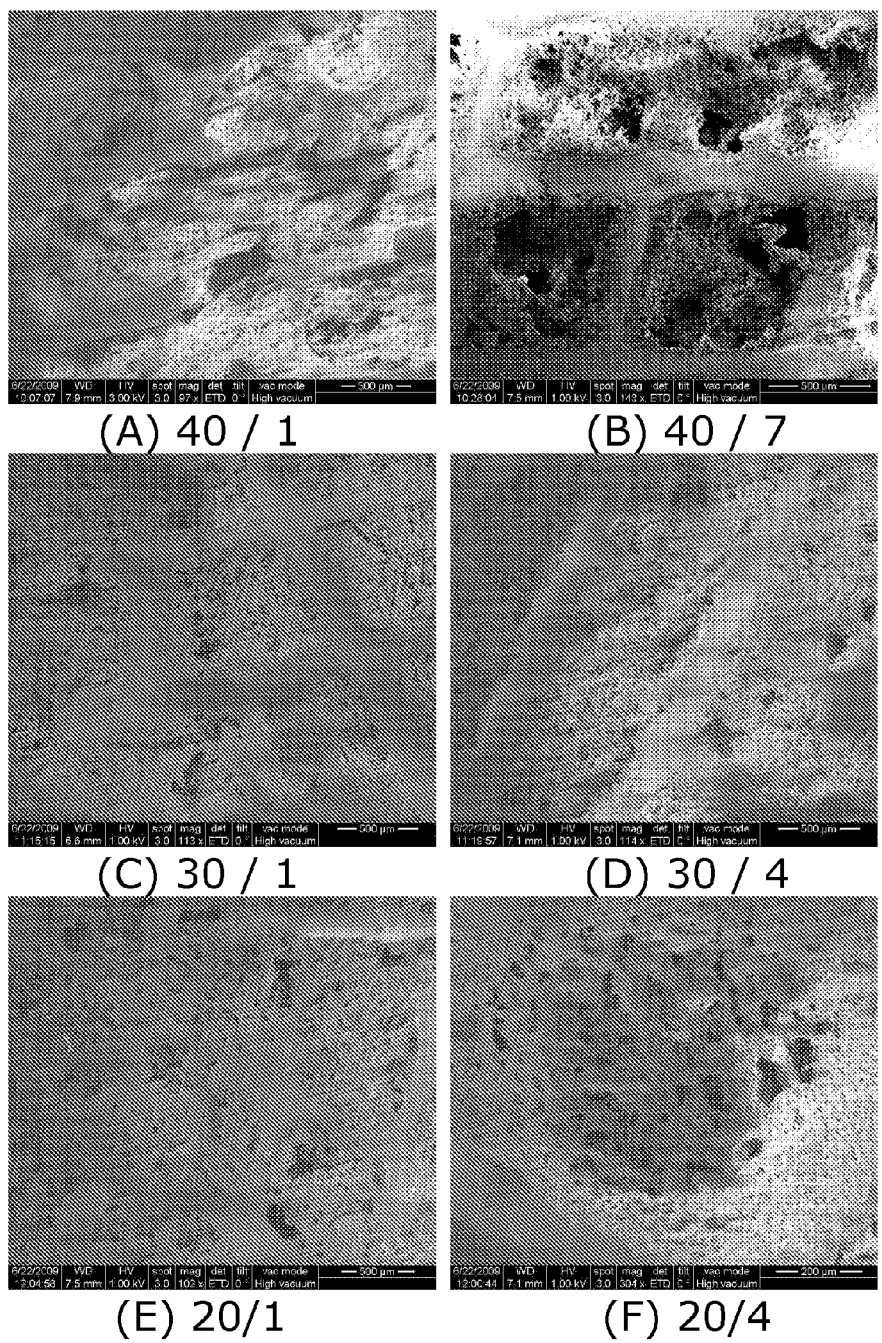
FIG. 19 shows plotted and freeze-dried (combined) scaffold. Fibre diameter ~175 μm, The used solution concentrations in mg (PCL)/g (Dioxane) and wt % of H2O are stated below each image.

To combine the best properties of both scaffold types, a printed and freeze-dried (combined) scaffold was manufactured. A printed PCL core was immersed in the dioxane-water-polymer solution before freezing and freeze-drying. The full range of polymer concentrations and wt % of H2O were tested according to the process window (FIG. 1) and it is possible to synthesize all previous structures within the plotted scaffolds (FIG. 19). Thereby, a mechanically stable scaffold featuring the excellent cell adhesion and ingrowth was obtained. High stiffness is provided by the plotted micron sized structure and is tuneable by the grid layout. Extremely high surface area and permeability is provided by the nano features introduced into the scaffold by the structures formed during the thermal induced phase separation. The features of the nano structure can be tuned by changing the concentration levels. It is central that the mechanisms used to tune macroscopic properties are not coupled to the mechanisms that can be used to tune the nanoscopic properties, so that properties can be tuned independently. These scaffolds could be formed in almost any 3D shape, because the printed structure determines the form and excessive freeze-dried material can be removed by forceps. This overcomes the rim-effect of the mould potentially closing the periphery of the scaffold for nutrient flow.

Figure 20:
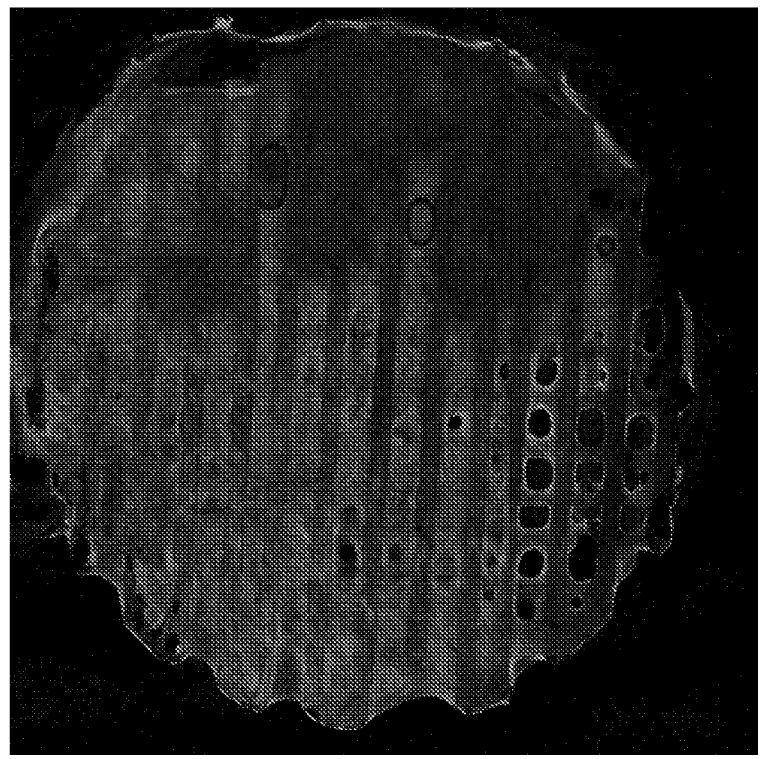
FIG. 20 shows live/dead staining of hMSC-TERT on combined scaffold.

Live/dead staining verified full cell viability also on the combined scaffolds (FIG. 20).

Highly stretched cells were observed on the PCL 0.07, whereas on the plotted PCL scaffolds, the cells seemed a little more rounded in morphology—perhaps because the surface of plotted PCL was smoother than the other scaffold surfaces.

In vitro Testing of Printed and Freeze-dried Scaffolds on Rabbit Cartilage Cells Printed and freeze-dried scaffolds were seeded with rabbit cartilage cells and the growth was compared to the commercial product Chondro-Gide® (CG) made from collagen type I and III.

The transcript levels of chondrogenic related genes (SOX 9, AGC, Col II and Col X) and osteogenic related genes Col I were assessed by qRT-PCR.

Real-time quantitative polymerase chain reaction (qRT-PCR) was performed under standard enzyme and cycling conditions on a 7500 fast real-time PCR system using TaqManC) gene expression assays (Applied Biosystems).

The expression of SOX 9 was twice as high for the seeded scaffold than for the CG.

The expression of Col II was four times higher for the seeded scaffold than for the CG.

The expression of AGC was five times higher for the seeded scaffold than for the CG.

The expression of Col X was equal to the seeded scaffold than for the cell scrape, indicating equal activity.

The expression of Col I was four times lower for the seeded scaffold than for the cell scrape, indicating less formation of scar tissue when the cells are growing in the scaffold.

Manufacturing of Macroencapsulated Printed Scaffolds

This study evaluated the effects of a printed scaffold coating and seeding system on cell seeding efficiency, proliferation, and differentiation. These parameters are most important for tissue engineering success. The coating system was a blend of both naturally derived and synthetic polymers and was applied on the scaffold along with the cells using a three-step process. We used an immortalized hMSC population to examine a PCL-based printed scaffold coated with hyaluronan, methlated-collagen and terpolymer via polyelectrolyte complex coacervation, under two different cultivation methods (spinner flask and static culture).

To improve the seeding efficiency and viability of bone marrow stromal cells (MSCs) in the 3D scaffold, macroencapsulation by polyelectrolyte complex coacervation was performed. The two polyelectrolytes used for the complex coacervation were methylated collagen and terpolymer of hydroxylethyl methacrylate, methyl methacrylate, and methacrylic acid (HEMA-MMA-MAA). By modulating the contact time, a collagen-terpolymer complex of different thickness and density of encapsulating the 3D scaffolds can be formed. The density of this hydrogel can be adjusted by controlling a number of parameters, such as the material properties of the polyelectrolyte pair, the contact time between the polyelectrolytes during the complex coacervation process, which could ensure effective cell entrapment without compromising mass transfer within the matrix.

Scaffold Manufacturing and Surface Treatment

Polycaprolactone (PCL) scaffolds were made by fused deposition modeling with a BioScaffolder (SYS+ENG GmbH, Germany). Cylindrical scaffolds with a diameter of 10 mm were punched out from a 5 mm thick porous PCL mats with a biopsy punch (Acuderm, Fla.). The overall fiber width and height was 170 and 120 µm, respectively. The center-center fiber distance in each deposited layer was 1.0 mm and the fiber orientation of each consecutive layer was angled 105° and shifted 0.17 mm. To increase surface hydrophilicity and thus improve cell attachment, the scaffolds underwent an ethanol and sodium hydroxide treatment regime that causes chain scission and end group hydroxylation of the superficial polymer chains. The scaffolds were rinsed in sterile water multiple times, dried and kept in a sterilized desiccator.

Methylated Collagen and Terpolymer Preparation

Cationic collagen was prepared by the esterification of the carboxyl groups using methanol (Chia, Leong et al. 2000). The concentration of methylated collagen was 3 mg/ml. Anionic terpolymer of HEMA-MMA-MAA was synthesized and purified as described elsewhere (Chia, Leong et al. 2000). Three percent terpolymer was used to macroencapsulate the 3D scaffolds.

Assembly and Characterization of the Co-polymeric Membranes on Scaffolds

The scaffolds were immersed in a 4.0 mg/ml hyaluronan solution (780 kDa, Lifecore Biomedical Inc., Lot P9805-9A) for 24 hours in an evacuated desiccator at room temperature, and were then freeze dried (Lyphoware, N.J., US). Macroencapsulation was done by pipetting 100 µl (micro liter) of 3 mg/ml of methylated collagen solution into the dried hyaluronan pre-coated scaffolds, and then covering with a final layer of 3% terpolymer solution. After 10 minutes of contact time, the complex coacervation reaction was quenched with phosphate buffered saline (PBS).

Scanning electron microscopy (SEM) was used to inspect the morphology and distribution of the co-polymer membranes on the scaffold.

Expansion of hMSC-TERT

A telomerase reverse transcriptase gene-transduced cell population, hMSC-TERT cells, was used in this study. These cells maintain their functional characteristics of primary MSCs and have the capability to differentiate into certain mesodermal cell types (osteoblasts, chondrocytes, and adipocytes) with specific stimuli. Cells from PD level 262 (passage 45) were seeded at a density of 4000 cells/cm$^2$ in culture flasks in Dulbecco's modified essential medium (DMEM) containing 10% fetal bovine serum (FBS) and cultivated in a humidified atmosphere of 37° C. and 5% $CO_2$. After one week cells were washed in PBS, detached with 1.25% trypsin and 5 mM EDTA in PBS, reseeded, and cultured for another week. Cells were trypsinized (PD level 271, passage 47) and resuspended for use (4×107 cells/mil) in DMEM/10% FBS (penicillin (100 µml) and streptomycin (100 mg/l).

Macroencapsulation of hMSC-TERT in PCL Scaffolds

Scaffolds coated with hyaluronan were placed in agarose-coated 6-well culture plates (4 scaffolds/well). 100 µl of 2×107 cells/ml cell suspension in 3 mg/ml solution of methylated collagen was dispensed onto scaffolds giving a seeding number of 1×106 cells/scaffold. Seeded scaffolds were incubated for 2 h and then encapsulated by 100 µl of 3% terpolymer solution in a drop-wise manner. After 10 minutes contact time, 7.5 ml DMEM/10% FBS, 100 µml penicillin, 100 mg/l streptomycin was added to each well and scaffolds were incubated overnight to allow the cells to attach. In the control group, uncoated PCL scaffolds were seeded with 1×106 cells/scaffold.

Spinner and Static Culture for Both Naked and Coated PCL Scaffolds

After 24 h, the scaffolds were either moved to new agarose-coated 6-well plates (1 scaffold/well) or placed in a 58 mm diameter dual side-arm spinner flask (Bellco glass, Vineland N.J., USA). An autoclavable steel framework with four needles was constructed and placed in the spinner flasks. Two cell-seeded scaffolds were placed on each needle giving a total of eight scaffolds per flask. Spinner flasks with 120 ml of media were placed on a Bell-ennium™ five position magnetic stirrer (Bellco Biotechnology, NJ, USA) with 4 mm magnetic bars at 30 rounds per minute in the $CO_2$ incubator with side arm caps loosely attached. From day one and thereafter, the media was DMEM/10% FBS with 10-8 M1,25-$(OH)_2$-vitamin D3 (Vit D, LEO Pharma, Denmark) for DNA, ALP, and gene expression analysis. On day 1, day 7, day 14, and day 21, four scaffolds from each group (uncoated and coated, static and spinner) were rinsed in PBS and frozen for DNA quantification; three scaffolds were collected for live/dead staining, histology, and SEM, and another four scaffolds were rinsed in cold PBS and frozen in 1 ml Trizol (Invitrogen, Taastrup, Denmark) for gene expression analysis. In addition, on day 7 and day 14, four scaffolds were used for ALP activity assay. The cell seeding efficiency was determined as % seeding efficiency=DNA amount per scaffold on day one/DNA amount of one million cells.

For calcium deposition measurement, scaffolds seeded with cells were cultured in DMEM/10% FBS for one week, and then medium was replaced with osteogenic stimulation media (DMEM/10% FBS with 100 nM dexamethasone, 290 µM ascorbic acid, and 5 mM β-glycerophosphate) (Sigma). On day 14, day 21, and day 28, four scaffolds from each group were collected for calcium assay and another scaffold for von Kossa staining. Media in all cultures were changed every 3-4 days.

DNA Quantification

The total cell number in the 3D cellular scaffold was estimated by quantifying the dsDNA content in each scaffold using the Quant-iT$^a$ PicoGreen® dsDNA assay (Invitrogen). Scaffolds were frozen in 1 ml MEM, thawed, and sonicated in intervals of 1 s on/5 s off for a total of 1 min. Three mg of collagenase were added to each DNA sample and the samples were incubated in a 37° C. water bath for 3 hours. 1 mg proteinase K was then added and the samples were incubated overnight in a 45° C. water bath. Sample volume was diluted 1:10 in Tris-EDTA buffer and vortexed to release DNA from scaffold debris. From each sample, 2×50 µl were drawn, prepared with PicoGreen®, incubated for 5 min in the dark, and measured in a 96-well plate using a microplate reader, Victor3 1420 Multilabel Counter, (PerkinElmer Life Sciences, Denmark). Samples were excited at 480 nm, and the fluorescence emission intensity was measured at 520 nm. Standards were prepared according to manufacturer's instruction (lambda DNA, concentration range: 0-1 µg/ml). Technical duplicates were used for each biological sample.

Live/Dead Staining

The scaffolds were rinsed in PBS and stained with 2 µM calcein AM and 4 µM ethidium homodimer (EthD-1) in PBS (LIVE/DEAD® Viability Kit, Molecular Probes) for 30 min in the dark. Non-fluorescent calcein AM is converted to highly fluorescent calcein by intracellular esterase activity and it stains viable cells green, whereas EthD-1 enters cells with injured membranes and stains dead cells red by binding to DNA. Images were acquired immediately using a laser scanning confocal microscope, 510 Meta (Zeiss Microimaging GmbH, Germany). The confocal settings (excitation, laser power, detector gain, and pinhole size) were same for all cell imaging. Separate channels and filters were used and excitation/emission wavelengths were 494/517 nm for calcein and 528/617 nm for EthD-1.

Alkaline Phosphatase (ALP) Activity Assay

ALP activity was determined using a colorimetric endpoint assay measuring the enzymatic conversion of p-nitrophenyl phosphate (Sigma) to the yellowish product p-nitrophenol in the presence of ALP. Absorbance of p-nitrophenol was measured by microspectrophotometer at excitation/emission: 405/600 nm. Standards were prepared from p-nitrophenol (concentration range: 0-0.2 mM). Technical duplicates were used for each biological sample.

Calcium Content Assay

Calcium contents of cell-seeded scaffolds were quantified by colorimetric endpoint assay based on the complexation of one $Ca^{2+}$ ion with two Arsenazo III molecules to a blue-purple product (Diagnostic Chemicals Limited, Charlottetown, PE, Canada). Briefly, the calcium deposition in dissolved in 1M acetic acid and placed in a shaker overnight. The samples were diluted from 1:50 with dd$H_2O$ and aliquots of 20 µl were transferred to a 96-well plate. Arsenazo III solution (280 ml) was added and incubated for 10 min at room temperature. A standard dilution series of calcium standard ranging from 0 to 50 µg/ml was prepared and $Ca^{2+}$ concentration was quantified spectrophotometrically at 650 nm. Calcium content was expressed as micrograms of $Ca^{2+}$.

Von Kossa Staining

Scaffolds were gently rinsed with PBS and fixation for five min in formaldehyde, then wash with dd$H_2O$, and incubated with a 2.5% silver nitrate solution for 20 min in the dark, and subsequently developed by adding hydroquinone for two min. Finally, surplus silver was removed using sodium thiosulphate for five min. Scaffolds were dried under vacuum and then took pictures. Then scaffolds were embedded in Technovit® 7100 (Ax-lab, Vedb3/4k, Denmark), and cut in 25 µm sections using a Sawing Microtome KDG 95 (Meprotech, Heerhugowaard, the Netherlands). Sections were stained with 0.1% toluidine blue. Images were viewed and photographed on a BX50 microscope with a digital camera (Camedia C-5060) (All products from Olympus, Denmark).

Histology

Scaffolds were fixed in 70% ethanol, Technovit® 7100 (Ax-lab, Vedb3/4k, Denmark) embedded, and cut in 25 µm sections using a Sawing Microtome KDG 95 (Meprotech, the Netherlands). Sections were taken from the peripheral and the central part of the scaffold, stained for 10 min at 37° C. with 1 mg/l Hoechst 33258 (Sigma-Aldrich, Brondby, Denmark) in PBS and mounted. Images were viewed and photographed on a BX50 Fluorescence microscope equipped with a WU 330-385 nm filter, and a digital camera (Camedia C-5060) (All products from Olympus, Denmark).

RNA Extraction and Real-time RT-PCR

Scaffolds collected in 1 ml Trizol were vortexed thoroughly; chloroform was added, and samples vortexed again. RNA was precipitated with isopropanol, washed with 75% ethanol and dissolved in RNase-free, DEPC-treated water (Ambion, Cambridgeshire, UK). RNA amount, purity and integrity were assessed using UV/vis spectrophotometry (absorbance at 260 and 280 nm) and agarose gel electrophoresis. The RNA samples were then treated with DNase I (Invitrogen). The cDNA was prepared from 2 µg of total RNA using the High Capacity cDNA Archive Kit (Applied Biosystems, Naerum, Denmark).

Real-time quantitative polymerase chain reaction (qRT-PCR) was performed under standard enzyme and cycling conditions on a 7500 fast real-time PCR system using Taq-Man® gene expression assays (Applied Biosystems) for Hs00427621_m1 (TATA box binding protein, TBP), Hs99999907_m1 (β-2-microglobulin, B2M), Hs99999908_m1 (glucuronidase β, GUSB), Hs00165814_m1 (SOX9), Hs00153936_m1 (Aggrecan, AGC), Hs00166657_m1 (Col X), Hs00231692_m1 (Runx2), Hs00758162_m1 (ALP), Hs00164004_m1 (collagen type I alpha I, Col I), Hs01587813_g1 (osteocalcin, OC), Hs00277762_m1 (osteonectin, ON), Hs00167093_m1 (bone sialoprotein I, BSP I/osteopontin, OP), Hs00173720_m1 (bone sialoprotein II, BSPII) and a custom designed Taq-Man® assay for human RNA polymerase II (RPII). These assays all include two unlabeled primers and one FAMTM dye-labeled TaqMan® MGB exonuclease probe spanning an exon boundary. Amplicon sizes were all less than 170 bp. Standard enzymes and cycling conditions for the 7500 Fast System were used. Template cDNA corresponding to 40 ng of RNA was added to each PCR reaction and each biological sample was run in technical duplicates for each gene. Data analysis was performed using 7500 Fast System Sequence Detection Software version 1.3. Expression levels of the genes of interest were normalized to a BestKeeper index (Pfaffl et al., 2004), calculated for each sample based on a geometric mean of threshold cycles (Ct) from GAPDH, UBC and RPII. The following equation was used for each sample:

Relative gene of interest expression=2 Ct (Best-Keeper)−Ct (gene of interest).

Statistical Analysis

Results are presented as mean±standard deviation (SD) for n=4 biological replicates.

Statistics were assessed using Stata 10.0 (College station, TX). The data of ALP activity, calcium content and gene expression were determined using two-way ANOVA (time× treatment). When significant main effects or an interaction between the main effects were found, specific comparisons were made with student t-tests (variance equal) or Wilcoxon rank-sum test (variance not equal). Differences between means were considered statistically significant when p-values <0.05.

Characterization of the Co-polymeric Membranes on Scaffolds

The SEM micrographs of the PCL scaffolds (not shown) show how the scaffolds are formed by the fusion of approximately 180 μm wide PCL fibers. With a center-center fiber spacing of 1 mm, the edge-edge distance between fibers in each layer is 640 μm. The uncoated fibers display a surface with 20-50 μm wide pits and shallow crevices, which are created during spherulite formation.

After scaffolds were macroencapsulated by polyelectrolyte complex coacervation, the hyaluronan—methylated collagen—terpolymer complex formed within and around the supporting grid (PCL scaffold). The co-polymer complex comprised of networks of nanofibers distributed homogeneously within the PCL scaffold, and supported by the PCL scaffold.

Cell Seeding Efficiency

Assuming that no cellular division occurred during the first 24 hours after seeding, the cell seeding efficiency was calculated to be 49.6% for the uncoated PCL scaffolds and 70.7% for the coated PCL scaffolds (t-test, p=0.0001, n=4).

DNA Quantification

DNA was extracted from the scaffolds because the DNA amount is proportional to the cell number. Thus, cell proliferation over time could be followed. During the culture period increasing amounts of DNA was observed in all cultures. For static culture, coated scaffolds had significantly higher DNA levels than uncoated scaffolds on day 7 (p=0.001) and day 14 (p=0.003). For dynamic culture, the uncoated scaffolds DNA levels were higher than the coated scaffolds' on day 7 (p=0.006) and day 14 (p=0.013). The DNA levels were higher in dynamic cultivation compared with static cultivation for both uncoated and coated scaffolds on day 14 and day 21.

Live/Dead Staining and Confocal Microscopy

The distribution of viable cells on the surface of scaffolds was visualized by confocal microscopy after staining by the live/dead fluorescent marker method. On day 1, the seeding resulted in a slightly irregular dispersion of cells on both coated and uncoated scaffolds. But by 7 days this was overcome in static cultures by cells proliferating and migrating to cover the whole scaffold surface for both coated and uncoated. However, the coated scaffolds showed a more homogeneously dispersed population of cells on the surface than the uncoated scaffolds at all the timepoints for static culture. For dynamic culture, a regularly dispersed cell layer was obtained on top of the scaffolds for both uncoated and coated on day 14 and day 21. The uncoated scaffold showed a more confluent cell layer compared with coated scaffold on day 14, but no difference on day 21. To compare static culture and dynamic culture, more confluent cell layers were obtained in the static culture—possibly due to cells migrate to the centre of the scaffolds in dynamic culture since the overall number of cells was not reduced compared with static culture.

ALP Activity

The ALP activity of the coated scaffolds was significantly higher than the uncoated scaffolds on day 7 and day 14 for both static and dynamic culture. ALP activity peaked earlier in the dynamic culture than the static culture.

Mineralization

To assess the mineralization of hMSC-TERT cells, the calcium contents of the cell/scaffold constructs were determined. Calcium deposition in the coated scaffolds was significantly higher than in the uncoated scaffolds on day 21 and day 28 for dynamic culture. There was no difference between uncoated and coated scaffolds in the static culture at all three time points. Dynamic spinner flask culture resulted in a significant increase in calcium deposition compared to the static culture for both uncoated and coated scaffolds on day 21 and day 28. It was 2.2 times and 3.5 times higher in the spinner cultured than the static cultured for uncoated group on day 21 and day 28, respectively. With the coating the increase was 4.6 times and 5.3 times higher.

We observed the darker von Kossa staining of the spinner cultured than the static cultured on both day 21 and day 28. The coated scaffolds had a more uniform black colour through the scaffolds than the uncoated ones. Regardless of the culture method, viable cells were present in the interior of the coated scaffolds. Cells penetrated deeper into the coated scaffolds than in the uncoated scaffolds for both static and spinner culture. Intense von Kossa staining in the coated scaffold under spinner culture suggested higher matrix mineralization.

Histology

Cellular distribution within the scaffold was evaluated by fluorescence microscopy cross-sections of the specimens. Pictures were taken from top to bottom of the scaffold across the central part of the whole scaffold section and merged using Photoshop CS3. After 7 days of culture, cells penetrated into the interior of the scaffolds and migrated to the fibers at the bottom. New ECM formation was observed on day 7 in the static and spinner constructs, most pronounced in the coated scaffolds under dynamic culture. After 14 days of culture, a noticeable amount of cells proliferated and migrated throughout the scaffold, which became more visible particularly after 3 weeks of cell culture. A clear difference between coated and uncoated scaffold was seen at day 21 of spinner culture. Cells were more spread out in the inter-fiber space across the coated construct compared to the uncoated.

Quantitative Real-time RT-PCR

The transcript levels of chondrogenic related genes (SOX 9, AGC and Col X) and osteogenic related genes Runx2, ALP, Col I, OC, ON, bone sialoprotein I (BSP I/OP), and bone sialoprotein II (BSP II) were assessed by qRT-PCR.

The expression of SOX 9 was higher for statically cultured constructs than spinner cultured constructs at all time points. For static culture, there was no difference between uncoated and coated scaffolds and the expression peaked at day 14. For spinner culture, the expression increased in coated scaffolds until day 7 and then remained stable.

Expression of AGC was higher in static culture than in spinner cultivation and coating reduced AGC expression in both statically and dynamically cultivated scaffolds.

Col X was highly expressed in spinner cultured scaffolds from day 7 and peaked at day 21, while the Col X expression was low in statically cultured scaffolds at all time points. The expression was higher in uncoated than in coated regardless of the cultivation methods.

Expression of Runx2 was higher for statically cultivated than spinner cultivated at all time points. For static culture, the expression reached a peak from day 14. For spinner culture, the expression increased by coating and peaked on day 21.

The expression of ALP was higher for statically cultivated than spinner cultivated at all time points. The expression was higher in coated than in uncoated regardless of the cultivation methods. The expression rose during culture in statically cultivated scaffolds, whereas a stable expression was observed in dynamically cultured ones.

The Col I expression increased significantly at day 21 for spinner cultivated scaffolds, but was otherwise stable at day 2 levels for both cultures.

OC expression was higher for statically cultivated than spinner cultivated from day 7.

For static culture, OC peaked at day 7 and decreased afterwards. OC was up-regulated by coating at most time points, by day 7 static culture, regardless of the cultivation methods.

ON expression was higher for spinner culture than for static culture. Coating down-regulated the expression at day 7 and day 14, but not at day 21 in both cultures.

The expression of BSPI (OP) decreased from day 2 in both static and spinner cultures. For static culture, coating always resulted in an up-regulated expression. As for the spinner cultures, the coating only up-regulated the expression at day 2.

BSPII expression was highest at day 2 and decreased considerably afterwards in both static and spinner cultures.

From the RT-PCR results, it can be seen that the gene transcription patterns for the uncoated spinner cultured scaffolds were rather remarkable for e.g. coil X, Runx2, and ALP. Collagen type X is a specific marker for chondrocyte hypertrophy, which is the final stage before final chondrocyte differentiation. Even though all culturing used osteogenic media, the ALP/DNA measurement makes it apparent that the osteogenic phenotype is the weakest in this group. These findings suggest that the cells in this group initiated endochondral ossification, in which an intermediate cartilage template is laid down and then calcified.

Conclusion

Coated PCL Scaffolds

Our study showed that the application of the Hyaluronan-Collagen-Terpolymer coating significantly improved all the outcome variables and furthermore seemed to have a dispersive effect on cell distribution within the porous scaffold. The effects of the coating come mainly from its crude mimicking of the natural ECM in the immediate surroundings of the cells. Hyaluronic acid and a derivative of type I collagen was used for this purpose as they are the major ECM constituents. Hyaluronic acid is a very large glycosaminoglycan present in most tissues. The size and hydrophilicity of the molecule are important properties for its function of adding turgor and mechanical resilience to tissues, especially those of the musculoskeletal system. At a molecular level, hyaluronan is the principal ligand for CD44, a ubiquitous transmembrane receptor that mediates both cell-cell and cell-matrix adhesion, in which CD44 is able to bind other ECM molecules like fibronectin and collagen. Pathways that determine cell morphology and survival can be triggered by CD44 receptor-ligand interactions. This is analogous to the effects of the integrin receptors and both receptor families converge on the activation of Ras and Rac.

Single cells in suspension retain a pericellular coat that is rich in hyaluronic acid. This coat mediates a fast integrin independent adhesion to the substrate. If the coat is enzymatically removed using hyaluronidase, the cells will bounce off the substrate even in the presence of integrin ligands. On the other hand, if both the substrate and the cell are covered in an abundance of hyaluronic acid, no integrin dependent attachment will take place and the cell will also bounce off. The attachment strength modulation is important during cell migration and cell division and the point is underlined by the increased tumor invasiveness when malignant cells have over-expression of hyaluronic acid or CD44. The rationale behind the coating procedure is that the inventors want to form a coacervation complex between the positively charged methylated collagen and the negatively charged hyaluronic acid coated scaffold surface. Such reaction would probably aid in bonding the collagen solution to the scaffold. The cells were mixed into the collagen solution rather than the hyaluronic acid, because the hyaluronic acid showed to be too viscous to make a homogeneous cell suspension. The final coating step was the application of the negatively charged terpolymer for encapsulation.

Generally, the results showed that scaffolds with coating have a higher cell seeding efficiency, higher number of differentiated cells, and are homogenously distributed. Qualitatively, the coating decreased the extent of cell sheet formation on the scaffold faces, which can limit nutrient transport. The ALP activity, calcium contents and the expression of several osteoblastic markers (e.g. ALP, OC, and BSP I) were significantly higher in the coated scaffolds. Spinner flasks were superior to static cultivation in terms of cell proliferation and survival, which were especially important for matrix mineralization. The present in vitro study provides evidence for the effectiveness of co-polymeric membranes on improving cellular seeding efficiency, increasing cellular penetration depth and improving cellular distribution in 3D scaffolds.

Manufacturing of Scaffolds Enabling Controlled Multi Lineage Differentiation of Stem Cells The creation of complex tissues and organs is the ultimate goal in tissue engineering. Engineered morphogenesis necessitates spatially controlled development of multiple cell types within an implant (scaffold). The inventors of the present invention present a novel solution for this requirement by adhering nanoparticles containing different small interfering RNAs (siRNAs) into nano-structured scaffolds. This allows spatial retention of the siRNAs within nanopores until their cellular delivery. The released siRNAs were capable of gene silencing BCL2L2 and TRIB2, in mesenchymal stem cells, enhancing osteogenic and adipogenic differentiation, respectively. Different nanoparticles localized to spatially distinct locations within a single implant allowed two different tissue types to develop in controllable areas of an implant. This simple yet effective approach for enhancing differentiation is immediately applicable to all areas of tissue engineering. Furthermore, the technique enables complex tissues and organs to be engineered by the in situ development of multiple cell types guided by spatially restricted nanoparticles.

The inventors present a novel technology, siRES (siRNA enhanced scaffolds), composed of biodegradable nano-structured poly-ε-caprolactone (PCL) scaffolds functionalized with a lyophilized polymer/lipid-based nanoparticulate siRNA delivery system. The particle localization and retention properties are investigated, as well as the silencing and in vitro and in vivo enhancement of differentiation of the system, using hMSCs as progenitor cells and siRNAs targeted to enhanced green fluorescent protein (EGFP), tribbles homolog 2 (TRIB2, also known as TRB2) and BCL2 like 2 (BCL2L2, also known as BCL-w). It is successfully demonstrated that enhancement of differentiation and, importantly, that tailored cell specialization can be affected differently in discrete locations within a composite scaffold by controlled deposition of BCL2L2 siRNA and TRIB2 siRNA containing nanoparticles.

Results
Monolayer Culture

The potential of reverse transfecting hMSCs with siRNA was initially studied in monolayer culture. Tissue culture plates coated by a lyophilization process with TransIT-TKO/siRNA particles with hydrodynamic diameter (259±14 nm) and zeta potential (12.6±0.5 mV) were seeded with telomerase immortalized hMSCs23. siRNA targeting EGFP (EGFP expressing hMSCs were used in this case 24), BCL2L2 and TRIB2 was used. Flow cytometry and quantitative PCR (qPCR) revealed that the delivery system was capable of reducing expression of all siRNA targeted genes by at least 50% after 2 days. EGFP protein levels were reduced by over 95% 7 days post transfection. The influence of the siRNA transfection on cell viability was studied by growing hMSCs 2 days on siRNA coated plates in maintenance medium followed by 12 days in various differentiation media. Transfected cell viability was slightly reduced (~30%, ~40% and ~45% reduction in viability for EGFP, TRIB2 and BCL2L2 siRNA) in maintenance medium. This reduction was comparable to that induced by differentiation medium. Using alkaline phosphatase and oil red o staining, hMSCs were shown to differentiate into osteoblastic and adipocytic lineages, respectively, when subjected to siRNA transfection and differentiation medium. In conclusion, freeze-dried TransIT-TKO/siRNA particles were an effective transfection agent for hMSCs in monolayer culture.

siRNA Coating of Scaffolds

Hierarchically organized scaffolds were produced through thermally induced phase separation of PCL in two solvents and nano-roughness and a hydrophilic surface was subsequently introduced by partial chemical degradation. When visualized with scanning electron microscopy (SEM) (not shown), the scaffolds appeared bimodal in pore size distribution. Large pores (diameter>50 μm) were separated by walls (thickness 10-40 μm) containing smaller cavities of decreasing size (the smallest structural features extended less than 15 nm. These nano-features greatly increase the surface area. When coated with nanoparticles, the smaller cavities were filled with siRNA nanoparticles with a maintained about 200 nm size range. In contrast, the protruding structures contained no visible nanoparticles. Fluorescent siRNA particles were adsorbed onto scaffolds to investigate particle adherence. When coated scaffolds were added media and serum, the siRNA continued to locate to the walls even after 24 hours (not shown). Scaffolds containing cells showed siRNA uptake, limited in a few cells up to 24 hours but in most of the population after 72 hours (not shown). The coating process resulted in deposition of intact adherent particles onto the scaffold walls and allowed siRNA internalization into seeded cells.

siRNA Induced Silencing on Scaffolds

To quantify knockdown, scaffolds were coated with particles containing EGFP siRNA and seeded with EGFP expressing hMSCs. After 48 hours, mRNA expression was measured by qPCR. EGFP expression was reduced on EGFP siRNA coated scaffolds (60% reduction compared to non-coated scaffolds, $p=0.02$, 35% reduction compared to scaffolds coated with mismatched siRNA, $p=0.05$). Next, hMSCs were seeded on scaffolds containing siRNA particles targeted to either BCL2L2 or TRIB2. After 72 hours mRNA expression was measured by qPCR. Both BCL2L2 siRNA and TRIB2 siRNA reduced the expression of BCL2L2 (40%, $p=0.004$) and TRIB2 (47%, $p=0.002$), respectively. In conclusion, the siRNA is taken up by cells and induces gene silencing.

siRNA Enhanced Differentiation on Scaffolds

To study whether siRES can influence differentiation, hMSCs were added to scaffolds pre-coated with siRNA against either TRIB2 or BCL2L2. Forty-eight hours after transfection in maintenance medium, adipogenic or osteogenic differentiation was induced using differentiation media. At various time points, samples were collected and subjected to qPCR, micro computed tomography and histological analysis.

In the adipogenic differentiation experiment, the expression of the early adipogenic marker, apolipoprotein 2 (aP2), the adipogenic transcription factor, PPARγ2, and the late adipogenic markers, adiponectin (ADN) and lipoprotein lipase (LPL), increased with time in non-coated scaffolds and eGFP or TRIB2 siRES. At day 7 the expression of all markers, except LPL, was specifically increased in the TRIB2 siRES compared to non-coated scaffolds (PPARγ2: 2.9 times higher, $p=0.03$. aP2: 2.8 times higher, $p=0.04$. ADN: 4.7 times higher, $p=0.01$).

In the osteogenic differentiation experiment, the expression of the early osteogenic marker, alkaline phosphatase (ALP), increased up to 140 fold peaking at day 7. At day 7 there was a higher expression of ALP in the BCL2L2 siRNA coated scaffolds than in the EGFP siRNA coated scaffolds (3.4 times higher, $p=0.004$). The expression of an alternative early osteogenic marker, collagen type I (COL1), decreased up to 80% during the experiment. However, the reduction was slowest in the BCL2L2 siRNA coated scaffolds, and COL1 levels were highest in this group at day 7 and 12 (Day 7: 2.1 times higher than EGFP siRNA coated, $p=0.01$. Day 12: 1.4 times higher than non-coated, $p=0.004$ and 1.3 times higher than EGFP siRNA coated, $p=0.002$). The expression of the late osteogenic marker, osteocalcin (OC), and the osteogenic transcription factor, RUNX2, increased during the timecourse with insignificant differences between the samples at day 7 and 14. At day 21 the expression of both genes had decreased in both controls, while remaining higher in the BCL2L2 siRNA coated scaffolds (RUNX2: 1.2 times higher than non-coated and 1.7 times higher than EGFP siRNA coated, $p=0.03$ and $p=0.02$, respectively. OC: 2.1 times higher than non-coated and 2.2 times higher than EGFP siRNA coated, $p=0.02$ and $p=0.03$, respectively).

Micro computed tomography, staining and immunohistochemistry was performed on siRES cultured in osteogenic medium for 21 days to confirm the qPCR findings. Micro computed tomography and von Kossa staining showed successful mineralization throughout the scaffolds, while osteocalcin immunohistochemistry demonstrated deposition of osteocalcin in the extracellular matrix. For all three assays, the bone matrix appeared most developed in the scaffolds coated with BCL2L2 siRNA. A negative control cultivated in maintenance medium showed no von Kossa or osteocalcin staining. Together, these in vitro results suggest that coating of scaffold implants with BCL2L2 siRNA increases their osteogenic development while TRIB2 siRNA coating enhances their adipogenic development.

To study the effect of siRNA coating on the development of tissue in vivo, the inventors subcutaneously implanted non-coated scaffolds as well as TRIB2 or BCL2L2 siRES into non-obese diabetic/severe combined immunodeficient (NOD/SCID) mice. Prior to implantation, the scaffolds were seeded with hMSCs for 16 hours. After 8 weeks the scaffolds were taken out and studied using immunohistochemistry and staining (not shown). All scaffolds showed neovascularization, and positive human-specific CD99 staining throughout the scaffolds confirmed that the majority of the cells were human. Positive staining with the early adipocytic marker S100 was only observed in the TRIB2 siRNA coated scaffolds indicating that silencing this gene allowed a subset of cells to start adipogenic differentiation. Collagen in the BCL2L2 siRNA coated scaffold was stained densely with Sirius red and birefringence under polarized light indicated it had a mature structure. In contrast, there was less intense birefringence and Sirius red staining in the non-coated control and almost no staining or birefringence in the TRIB2 siRNA coated scaffolds. Furthermore, collagen type I specific staining supported the Sirius red findings confirming that the deposited collagen was osteogenic type one. Osteonectin and RUNX2 staining were more pronounced in the BCL2L2 siRNA coated scaffolds than in the non-coated scaffolds which again were more positively stained than the TRIB2 siRNA coated scaffolds. No evidence of mineralization, however, was observed. These in vivo results confirm the in vitro findings but the cells did not terminally differentiate into osteoblasts at the subcutaneous site of implantation with siRNA as the only differentiation cue.

Dual Differentiation in Scaffolds

To construct a tissue with two cell types, scaffold cylinders were cut in half and each part was coated with TRIB2 or BCL2L2 siRNA. The two sides were then joined together and hMSCs were added.

For in vitro testing, the scaffolds were cultured 2 days in maintenance medium and 8 days in complex differentiation medium. The two sides were then separated and the mRNA levels of differentiation markers measured for each part. The expression of PPARγ2, RUNX2, ADN and OC within statistical variations equal in the two sides. However, aP2 was nearly 4 fold up-regulated in the TRIB2 siRNA coated part, and ALP was 45% up-regulated in the BCL2L2 siRNA coated part. For in vivo evaluation, the combined scaffolds were seeded with hMSCs, cultured 16 hours in maintenance medium and implanted subcutaneously for 2 weeks in mice. The scaffolds were then surgically removed, sectioned and stained using H&E, Sirius red and von Kossa staining. Visualization with H&E revealed that both scaffold parts contained cells but had developed very different morphologies. The BCL2L2 siRNA coated side appeared dense whilst the TRIB2 siRNA coated side was spongy with large holes. The Sirius red staining showed extensive deposition of organized birefringent collagen under polarized light in the BCL2L2 siRNA coated side, whilst no birefringence was observed in the TRIB2 siRNA coated side. The von Kossa staining showed no mineralization in either side. These results indicate that cells can be induced to commit to alternative differentiation pathways in specific locations within the same implant in vitro and in vivo by placing different siRNAs in distinct locations.

Discussion

This work presents a nanoparticle decorated nano-structured scaffold, capable of retaining and delivering siRNA, with broad applications for controlling stem cell differentiation in vitro and in vivo. When functionalized with two different siRNAs such a scaffold was shown to promote two alternative differentiation pathways in specific locations, both in vitro and in vivo.

siRNA has previously been delivered to cells growing within a three-dimensional matrix either by embedding the siRNA in flexible hydrogels or by adding the siRNA to the culturing medium, alternatively, cells have been transfected with siRNA prior to seeding onto implants. None of these methods, however, is applicable to delivery of siRNA in specific locations in order to generate multiple cell types within a matrix. This necessitates stable binding of siRNA to scaffold walls until subsequent delivery directly to attaching cells.

DNA delivery from scaffolds has been explored more extensively than siRNA. These studies have been performed by adsorbing naked plasmid DNA, DNA containing nanoparticles and viral vectors onto scaffolds. The transfection efficiency of naked nucleic acids is usually very low and naked siRNA delivery is further complicated by instability to RNases. As viral vectors have disadvantages due to oncogenicity and immunogenicity, non-viral vectors offer an attractive delivery solution. Lyoprotected, dried siRNA nanoparticles can normally achieve high silencing but common lyoprotectants, such as glucose, can induce adipogenic differentiation. Importantly, TransIT-TKO/siRNA complexes can be freeze-dried without a lyoprotectant, stored dry for prolonged periods and still retain high knockdown efficiency in serum promoting their use for scaffold delivery. When lyophilized onto the scaffolds, the nanoparticles retained their pre-lyophilization morphology and located to the smaller cavities within the scaffold walls. NaOH treated PCL is negatively charged because of exposed carboxylic acid and the inventors found TransIT-TKO/siRNA nanoparticles to be positively charged. The observed interaction is therefore most likely electrostatic in nature. The nano-structured holes presumably provide a greatly increased surface area with which the cationic TransIT-TKO component can interact through multiple ionic interactions. Furthermore, these nano-pores can be expected to protect against fluid flow displacement. The stability of the interaction is indicated by the continued retention of the nanoparticles in the walls after 24 hours in serum containing medium. This stable adherence enables localization of siRNA nanoparticles and the regional knockdown they induce.

In vitro, the inventors observed that BCL2L2 silencing enhanced osteogenic differentiation when combined with osteogenic medium. In vivo, the inventors found no evidence of mineralization, confirming previously published in vitro findings that BCL2L2 knockdown alone does not induce mineralization. However, the inventors did find that BCL2L2 knockdown alone enhanced early osteogenic differentiation with regard to collagen type I deposition and organization in vivo. TRIB2 silencing increased adipogenic differentiation in vitro when combined with adipogenic medium. This confirms several in vitro monolayer studies demonstrating that the TRIB family members repress adipogenic differentiation. TRIB2 inhibits adipogenesis by inhibiting Akt1 activation while increasing C/EBP degradation. EGFP-specific siRNA appeared to increase adipogenic differentiation, although not as much as TRIB2 siRNA. The in vivo study showed that TRIB2 knockdown alone was enough to abolish collagen birefringence while allowing a subset to differentiate into s100 positive adipocytes after 8 weeks. The inventors speculate that one siRNA, while enhancing differentiation, is insufficient to drive terminal osteogenic and adipogenic specialization without further stimuli. The few S100 positive adipocytes observed in vivo, may be a result of a weak adipogenic stimulus from the scaffolds or the implantation site. Without differentiation media, it may require multiple siRNAs to complete differentiation 14. Alternatively, microRNAs (miRNAs) or miRNA inhibitors (antimirs) could be used. miRNAs are endogenous RNA molecules related to siRNAs, and they simultaneous regulate multiple genes. miRNAs increasing osteogenic and adipogenic differentiation have been found. Considering that the TransIT-TKO delivery system can deliver miRNA and antimirs, the system presented here should also be directly applicable for scaffold delivery of miRNA regulators.

The inventors were able to develop a nano-structured scaffold that preferentially stimulated adipocytic and osteoblastic differentiation in distinct regions using localized coating with siRNAs against TRIB2 and BCL2L2. This was confirmed in vitro by the differential expression of the markers aP2 and ALP. Furthermore, the morphology of the two adjacent parts was markedly different in the in vivo incubated scaffolds and collagen deposition and organization was highly increased in the BCL2L2 coated side. Whilst the inventors have focused on siRNA nanoparticles due to known versatility, spatial localization of other differentiation cues could possibly be used to achieve the same result. In addition, other assembly techniques such as rapid prototyping of different drugs to distinct locations could conceivably be used instead of manually assembling building blocks.

The inventors have developed an example of a nanoparticle functionalized scaffold capable of delivering siRNA to seeded cells. Further, the inventors have demonstrated that the siRNA induces sequence specific gene silencing in these cells. As clinically relevant examples, the inventors have shown that specific targeting of TRIB2 and BCL2L2 leads to enhanced adipogenic and osteogenic differentiation, respectively. Scaffold coating with a single type of siRNA is thus a versatile and effective method for enhancing the development of single cell type tissues and represents a method for conducting gene knockout studies in 3D. Importantly, the nano-structured nature of the scaffolds enables nanoparticle retention and localization of different siRNAs to distinct parts of an implant. This made it possible to guide stem cells into alternate differentiation in specified locations.

References

R. G. J. C. Heijkants et al., *Polyurethane scaffold formation via a combination of salt leaching and thermally induced phase separation*, J. Biomedicinal Materials Research Part A (2008).

Chia, S. M., K. W. Leong, et al., *Hepatocyte encapsulation for enhanced cellular functions*, Tissue Eng 6(5): 481-95 (2000).

E. B. Antonio Ascenzi, *The compressive properties of single osteons*, The Anatomical Record, vol. 161, pp. 377-391, (1968).

Engler et al. Matrix elasticity directs stem cell lineage specification. Cell (2006) vol. 126 (4) pp. 677-689

The invention claimed is:

1. A three-dimensional biocompatible scaffold comprising a first and a second biocompatible material, said first material shaped as one or more grids of micron sized strands forming an open network of voids, said second material filling the voids of said open network, said second material being porous, wherein the pores are interconnected, said second material having a plurality of open cells substantially uniformly distributed therein, wherein the average size of said open cells is 1 nm to 6 micrometer, said grid providing protective mechanical support of the second biocompatible material, said grid further protecting the three-dimensional biocompatible scaffold against compressive forces during preparation, insertion and use, and said second biocompatible material comprising one or more biocompatible polymers, wherein the initial compressive stiffness of the grid is 5-100000 times higher than the initial compressive stiffness of the second biocompatible material.

2. The three-dimensional biocompatible scaffold according to claim 1, wherein the stiffness of the grid is 15-90000 times higher than the second biocompatible material.

3. The three-dimensional biocompatible scaffold according to claim 1, wherein the initial compressive stiffness of the grid when in combination with the first biocompatible material is within the range of 360-5100 kPa.

4. The three-dimensional biocompatible scaffold according to claim 1, wherein the initial compressive stiffness of the second biocompatible material is within the range of 0.31-6.32 kPa.

5. The three-dimensional biocompatible scaffold according to claim 1, wherein the scaffold has a comparable value of compression stiffness to the value of compression stiffness of the targeted tissue.

6. The three-dimensional biocompatible scaffold according to claim 1, having compatible compression strength to withstand the compressive pressure from the surrounding targeted tissue.

7. The three-dimensional biocompatible scaffold according to claim 1, having a compression stiffness of 4 GPa, 17 GPa, 1 GPa, 3 kPa, 1.9 kPa, 275 kPa, 800 kPa, 100 kPa, 600 kPa or 45 kPa.

8. The three-dimensional biocompatible scaffold according to claim 1, wherein the scaffold surface is coated with a natural or synthetic coating material.

9. The three-dimensional biocompatible scaffold according to claim 1, wherein the open cells are of an average size of 1 nanometer to 1 micrometer.

10. The three-dimensional biocompatible scaffold according to claim 1, wherein the cell density of said open cells in said second material is lying in a range from about $10^9$ to about $10^{15}$ open cells per cubic centimeter of said second material.

11. The three-dimensional biocompatible scaffold according to claim 1, wherein the total volume of the open cells formed in said second material comprise a fractional percentage of the total volume of said second material, which lies within a range from about 20 to about 90 fraction percent.

12. The three-dimensional biocompatible scaffold according to claim 1, wherein the average diameter of the pores formed in said second material being 0.01 to 800 micrometers.

13. A method for implanting a tissue scaffold comprising:
providing the tissue scaffold of claim 1; and
implanting said tissue scaffold in a subject in need of tissue regeneration.

14. A three-dimensional biocompatible scaffold comprising a first and a second biocompatible material, said first material shaped as one or more grids of micron sized strands forming an open network of voids, said second material filling the voids of said open network, said second material being porous, wherein the pores are interconnected, said second material having a plurality of open cells substantially uniformly distributed therein, wherein the cell density of said open cells in said second material is from $10^9$ to $10^{20}$ open cells per cubic centimeter of said second material, said grid providing protective mechanical support of the second biocompatible material, said grid further protecting the three-dimensional biocompatible scaffold against compressive forces during preparation, insertion and use, and said second biocompatible material comprising one or more biocompatible polymers, wherein the initial compressive stiffness of the grid is 5-100000 times higher than the initial compressive stiffness of the second biocompatible material.

15. A three-dimensional biocompatible scaffold comprising a first and a second biocompatible material, said first material shaped as one or more grids of micron sized strands forming an open network of voids, said second material filling the voids of said open network, said second material being porous, wherein the pores are interconnected, said second material having a plurality of open cells substantially uniformly distributed therein, wherein the total volume of the cells in said second material comprise a fractional percentage of the total volume of said second material, which lies within a range from about 10 to about 99 fraction percent, said grid providing protective mechanical support of the second biocompatible material, said grid further protecting the three-dimensional biocompatible scaffold against compressive forces during preparation, insertion and use, and said second biocompatible material comprising one or more biocompatible polymers, wherein the initial compressive stiffness of the grid is 5-100000 times higher than the initial compressive stiffness of the second biocompatible material.

* * * * *

UNITED STATES PATENT AND TRADEMARK OFFICE
CERTIFICATE OF CORRECTION

PATENT NO. : 8,815,276 B2  
APPLICATION NO. : 13/377430  
DATED : August 26, 2014  
INVENTOR(S) : Jens Vinge Nygaard Page 1 of 1

It is certified that error appears in the above-identified patent and that said Letters Patent is hereby corrected as shown below:

On the Title Page

In column 2 (page 1, item 56) at line 9, Under Other Publications, change "Polyrethane" to --Polyurethane--.

In the Specification

In column 4 at line 37, Change "days" to --15 days--.

In column 7 at line 53, Change "to" to --15 to--.

In column 14 at line 47, Change "groupsto" to --groups to--.

In column 15 at line 10, Change "Fluansione," to --Fluanisone,--.

In column 17 at line 21, Change "FIG. 11)" to --FIG. 11).--.

In column 19 at lines 1-2, Change "TagManC)" to --TagMan®--.

In column 19 at line 23, Change "methlated" to --methylated--.

In column 20 at line 27, Change "mil)" to --ml)--.

In column 20 at line 28, Change "μml)" to --U/ml)--.

In column 20 at line 37, Change "μml" to --U/ml--.

In column 27 at line 9, Change "case 24)," to --case24),--.

Signed and Sealed this  
Seventh Day of July, 2015

Michelle K. Lee  
*Director of the United States Patent and Trademark Office*